US009549970B2

(12) United States Patent
Franzusoff et al.

(10) Patent No.: US 9,549,970 B2
(45) Date of Patent: Jan. 24, 2017

(54) METHODS FOR PRODUCING YEAST-BASED VACCINES

(71) Applicant: GlobeImmune, Inc., Louisville, CO (US)

(72) Inventors: Alex Franzusoff, Nahant, MA (US); Deborah Quick, Louisville, CO (US)

(73) Assignee: GlobeImmune, Inc., Louisville, CO (US)

( * ) Notice: Subject to any disclaimer, the term of this patent is extended or adjusted under 35 U.S.C. 154(b) by 324 days.

(21) Appl. No.: 13/798,725

(22) Filed: Mar. 13, 2013

(65) Prior Publication Data
US 2013/0309269 A1 Nov. 21, 2013

Related U.S. Application Data

(63) Continuation of application No. 12/525,045, filed as application No. PCT/US2008/052843 on Feb. 1, 2008, now Pat. No. 9,066,893.

(60) Provisional application No. 60/899,281, filed on Feb. 2, 2007.

(51) Int. Cl.
A61K 39/00 (2006.01)
A61K 36/064 (2006.01)
A61K 39/39 (2006.01)

(52) U.S. Cl.
CPC ............ A61K 39/00 (2013.01); A61K 36/064 (2013.01); A61K 39/39 (2013.01); A61K 2039/57 (2013.01); C07K 2319/00 (2013.01); C07K 2319/035 (2013.01); C12N 2760/18634 (2013.01)

(58) Field of Classification Search
None
See application file for complete search history.

(56) References Cited

U.S. PATENT DOCUMENTS

| 4,775,622 | A | 10/1988 | Hitzeman et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |
| 7,083,787 | B2 | 8/2006 | Duke et al. |
| 7,439,042 | B2 | 10/2008 | Duke et al. |
| 7,465,454 | B2 | 12/2008 | Franzusoff et al. |
| 7,563,447 | B2 | 7/2009 | Franzusoff et al. |
| 7,595,060 | B2 | 9/2009 | Duke et al. |
| 7,625,569 | B2 | 12/2009 | Duke et al. |
| 7,632,511 | B2 | 12/2009 | Duke et al. |
| 7,736,642 | B2 | 6/2010 | Duke et al. |
| 7,745,128 | B2 | 6/2010 | Guo et al. |
| 8,007,816 | B2 | 8/2011 | Duke et al. |
| 2003/0035810 | A1 | 2/2003 | Caplan |
| 2007/0172503 | A1 | 7/2007 | Selitrennikoff et al. |
| 2008/0003239 | A1* | 1/2008 | Duke et al. ............... 424/206.1 |
| 2009/0098154 | A1 | 4/2009 | Franzusoff et al. |
| 2009/0142366 | A1 | 6/2009 | Franzusoff et al. |
| 2009/0142367 | A1 | 6/2009 | Franzusoff et al. |
| 2009/0304741 | A1 | 12/2009 | Duke et al. |
| 2010/0034840 | A1 | 2/2010 | Apelian et al. |
| 2010/0104604 | A1 | 4/2010 | Selitrennikoff et al. |
| 2010/0111912 | A1 | 5/2010 | Apelian et al. |
| 2010/0150963 | A1 | 6/2010 | Duke et al. |
| 2010/0189749 | A1 | 7/2010 | Franzusoff et al. |
| 2010/0196411 | A1 | 8/2010 | Duke et al. |
| 2010/0215678 | A1 | 8/2010 | Guo et al. |
| 2011/0150909 | A1 | 6/2011 | Franzusoff et al. |
| 2011/0301329 | A1* | 12/2011 | Van Urk et al. ............... 530/369 |

FOREIGN PATENT DOCUMENTS

| EP | 0414404 | 2/1991 |
| FR | 2486400 | 1/1982 |
| JP | 05-9124 | 1/1993 |
| JP | 06-277086 | 10/1994 |
| JP | 2002-291480 | 10/2002 |
| JP | 2007-863 | 1/2007 |
| KR | 10-0507665 | 8/2005 |
| WO | WO 98/35049 | 8/1998 |
| WO | WO 2008/115610 | 9/2008 |
| WO | WO 2010/033841 | 3/2010 |
| WO | WO 2010/065626 | 6/2010 |
| WO | WO 2010/121180 | 10/2010 |
| WO | WO 2011/032119 | 3/2011 |
| WO | WO 2011/115914 | 9/2011 |

OTHER PUBLICATIONS

Notice of Allowance with English Translation for China Patent Application No. 200880010797.6, dated Mar. 25, 2014 4 pages.
Intention to Grant for European Patent Application No. 08714176.8, dated May 2, 2014 7 pages.
Notice of Allowance with English Translation for Japan Patent Application No. 2009-548478, dated May 27, 2014 2 pages.
Official Action with English Translation for Taiwan Patent Application No. 096103983, dated Mar. 21, 2014 8 pages.
Decision to Grant for European Patent Application No. 08714176.8, dated Sep. 18, 2014 2 pages.
Official Action for India Patent Application No. 5607/DELNP/2009, dated Dec. 17, 2014 3 pages.
Official Action for U.S. Appl. No. 12/525,045, mailed Jan. 15, 2015 9 pages.
Ausubel, F.M. et al. eds. (2001). Current Protocols in Molecular Biology, vol. 1, John Wiley & Sons, Inc., Supplement 55, pp. 1-11, (Table of Contents Only.).

(Continued)

Primary Examiner — Robert A Zeman
(74) Attorney, Agent, or Firm — Sheridan Ross P.C.; Angela Dallas Sebor

(57) ABSTRACT

The invention provides methods for culturing yeast at a neutral pH level. Yeast cultured under neutral pH conditions exhibit desirable characteristics useful for biological purposes, such as the development of vaccines, prophylactics and therapeutics. The invention also provides for composi- (Continued)

tions and kits comprising yeast grown using the methodologies disclosed herein.

23 Claims, 9 Drawing Sheets

(56) References Cited

OTHER PUBLICATIONS

Barnett, J.A. (Jun. 6, 2008). "A History of Research on Yeasts 12: Medical Yeasts Part 1, Candida albicans," Yeast 25(6):385-417.
Beaucage, S.L. et al. eds. (2000). Current Protocols in Nucleic Acid Chemistry, John Wiley & Sons, Inc: New York, NY, Supplement 37, pp. 1-7, (Table of Contents Only.).
Bizzini, B. et al. (1990). "Use of Live *Saccharomyces cerevisiae* Cells as a Biological Response Modifier in Experimental Infections," FEMS Microbiol. Immunol. 64(3):155-167.
Brake et al. "a-Factor-directed synthesis and secretion of mature foreign proteins in *Saccharomyces cerevisiae*." PNAS, Aug. 1984, vol. 81, pp. 4642-4646.
Brenner, C. et al. (Feb. 1992). "Structural and Enzymatic Characterization of a Purified Prohormone-Processing Enzyme: Secreted, Soluble Kex2 Protease," Proc. Natl. Acad. Sci. 89:922-926.
Broach, J.R. et al. eds. (1991). Genome Dynamics, Protein Synthesis, and Energetics the Molecular and Cellular Biology of the Yeast *Saccharomyces*, Cold Spring Harbor Laboratory Press: Plainview, NY, pp. v, (Table of Contents Only.).
Chu et al. "Fermentation Process Optimization of Recombinant *Saccharomyces cerevisiae* for the Production of Human Interferon-a2a," Applied Biochemistry and Biotechnology Part A, 2003, vol. 111, No. 3, pp. 129-137.
Cohen, J. (Jun. 17, 1994). "Will Media Reports KO Upcoming Real-Life Trials?" Science 264:1660.
Cohen, J. (Jun. 24, 1994). "U.S. Panel Votes to Delay Real-World Vaccine Trials," Science 264:1839.
Engelhardt, J.F. et al. (Oct. 1994). "Prolonged Transgene Expression in Cotton Rat Lung with Recombinant Adenoviruses Defective in E2a," Human Gene Therapy 5(10):1217-1229.
Eto et al. Immunization with Recombinant *Escherichia coli* Expressing Retinal S-Antigen-Induced Experimental Autoimmune Uveitis (EAU) in Lewis Rats, Cellular Immunology, Mar. 1993, vol. 147, No. 1, pp. 203-214.
Fattal-German, M. et al. (1992). "Assessment of the Anti-Viral Effect of a Short-Term Oral Treatment of Mice with Live *Saccharomyces cerevisiae* Cells," Dev. Biol. Stand. 77:115-120.
Franzusoff, A. et al. (Apr. 1, 2005). "Yeasts Encoding Tumour Antigens in Cancer Immunotherapy," Expert Opinion on Biological Therapy 5(4):565-575.
Franzusoff, A. et al. (Feb. 17, 1995). "Biochemical and Genetic Definition of the Cellular Protease Required for HIV-1 gp160 Processing," The Journal of Biological Chemistry 270(7):3154-3159.
Fujita et al. "Studies in the development of Japanese encephalitis vaccine: expression of virus envelope glycoprotein V3 (E) gene in yeast." Bulletin of the World Health Organization, Feb. 1987, vol. 65, No. 3, pp. 303-308.
Guthrie, C. et al. eds. (1991). "Guide to Yeast Genetics and Molecular Biology," vol. 194 in Methods in Enzymology, Academic Press, Inc: San Diego, CA, pp. v-ix, (Table of Contents Only).
Haller, A.A. et al. (Feb. 9, 2007). "Whole Recombinany Yeast-Based Immunotherapy Induces Potent T Cell Responses Targeting HCV NS3 and Core Proteins," Vaccine 25(8):1452-1463.
Harlow, E. et al. (1988). Antibodies, A Laboratory Manual, Cold Spring Harbor Laboratory: Cold Spring Harbor, NY, pp. iii-ix, (Table of Contents Only.).
Harlow, E. et al. (1999). Using Antibodies. A Laboratory Manual, Cold Spring Harbor Laboratory Press: Cold Spring Harbor, NY, pp. 1-5, (Table of Contents Only.).
Jones, E.W. et al. eds. (1992). Gene Expression the Molecular and Cellular Biology of the Yeast *Saccharomyces*, Cold Spring Harbor Laboratory Press: Plainview, NY, pp. v-vi, (Table of Contents Only.).
Kim et al. "Culture Method to Enhance the Productivity of Hepatitis B Surface Antigen (pre S3 + S Ag) With Recombinant *Saccharomyces cerevisiae*," Biotechnology Techniques, Apr. 1996, vol. 10, pp. 233-238.
Klepfer et al. "Characterization of rabies glycoprotein expressed in yeast." Archives of Virology, 1993, vol. 128, No. 3-4, pp. 269-286.
Lu, Y. et al. (Aug. 1, 2004). "Mutation-Selective Tumor Remission with Ras-Targeted, Whole Yeast-Based Immunotherapy," Cancer Research, 64:5084-5088.
Matousek, J.L. et al. (Jan. 2003). "Evaluation of the Effect of pH on in vitro Growth of Malassezia pachydermatis," Canadian Journal of Veterinary Research 67(1):56-59.
Moore et al. "Novel yeast-based vaccine against HIV-SF2 gp160 promotes a cytotoxic 43-62 cell response." FASEB Journal 1996, vol. 10, No. 6, p. A1473 ZP002186594.
Mullis, K.B. et al. (1994). The Polymerase Chain Reaction, Birkhauser: Boston, MA, pp. xv-xvii, (Table of Contents Only.).
Plotkin, SA et al. (1999). Vaccines. Third Edition, W.B. Saunders Company: Philadelphia, PA, pp. xvii-xix, (Table of Contents Only.).
Pringle, J.R. et al. eds. (1997). Cell Cycle and Cell Biology The Molecular and Cellular Biology of the Yeast *Saccharomyces*, Cold Spring Harbor Laboratory Press: Plainview, NY, pp. v-vi, (Table of Contents Only.).
Rabinovich, N.R. et al. (Sep. 2, 1994). "Vaccine Technologies: View to the Future," Science 265:1401-1404.
Romani, L. et al. (Feb. 1, 1993). "CD4+ Subset Expression in Murine Canadidiasis Th Responses Correlate Directly with Genetically Determined Susceptibility or Vaccine-Induced Resistance," Journal of Immunology, 150(3):925-931.
Rose, M.D. et al. (1990). Methods in Yeast Genetics, A Laboratory Course Manual, Cold Spring Harbor Laboratory Press: Plainview, NY, pp. iii-iv, (Table of Contents Only.).
Sambrook, J. et al. (1989). Molecular Cloning, A Laboratory Manual. Second Edition, Cold Spring Harbor Laboratory Press: Plainview, NY, pp. xi-xxxviii, (Table of Contents Only.).
Sambrook, J. et al. (1989). Molecular Cloning, A Laboratory Manual. Third Edition, Cold Spring Harbor Laboratory Press: Cold Spring Harbor, NY, pp. v-xx, (Table of Contents Only.).
Schreuder et al. "Yeast expressing hepatitis B virus surface antigen determinants on its surface: implications for a possible oral vaccine." Vaccine, Apr. 1996, vol. 14, No. 5, pp. 383-388.
Serrano, R. et al. (Dec. 2002). The Transcriptional Response to the Alkaline pH in *Saccharomyces cerevisiae*: Evidence for Calcium-Mediated Signalling, Molecular Microbioloqy 46(5): 1319-1333.
Sheng et al. "Mannan derivatives induce phenotypic and functional maturation of mouse dendritic cells," Immunology, Jul. 2006, vol. 118, No. 3, pp. 372-383.
Sinai et al. "Enhancement of Resistance to Infectious Diseases by Oral Administration of Brewers Yeast," Infection and Immunity, May 1974, vol. 9, No. 5, pp. 781-787.
Skinner, FA et al. eds. (1980). Biology and Activities of Yeasts the Society for Applied Bacteriology Symposium Series No. 9, Academic Press Inc: New York, NY, pp. ix-xii, (Table of Contents Only.).
Stubbs, A.C. et al. (May 2001). "Whole Recombinant Yeast Vaccine Activates Dendritic Cells and Elicits Protective Cell-Mediated Immunity," Nature Medicine 7(5):625-629.
Valenti, P. et al. (1986). "Interaction Between Lactoferrin and Ovotransferrin and Candida Cells," FEMS Microbiology Letters 33(2-3):271-275.
Valenzuela et al. "Antigen engineering in yeast: Synthesis and assembly of hybrid hepatitis B surface antigen-Herpes simplex 1 gD particles," Bio/Technology, Apr. 1985, vol. 3, pp. 323-326.
International Search Report for International (PCT) Patent Application No. PCT/US2008/052843, mailed Sep. 22, 2008 4 pages.
International Preliminary Report on Patentability for International (PCT) Patent Application No. PCT/US2008/052843, issued Aug. 4, 2009 7 pages.

(56) References Cited

OTHER PUBLICATIONS

Official Action for Australia Patent Application No. 2008214029, dated May 18, 2012 2 pages.
Official Action with English translation for China Patent Application No. 200880010797.6, issued Nov. 24, 2011 10 pages.
English Translation of Official Action for China Patent Application No. 200880010797.6, dated Jul. 30, 2012 4 pages.
English Translation of China Patent Application No. 200880010797.6, dated Apr. 16, 2013 5 pages.
Examination Report mailed on Aug. 23, 2010, for European Patent Application No. 08714176.8, filed on Feb. 1, 2008, 6 pages.
Examination Report mailed on Jan. 25, 2010, for European Patent Application No. 08714176.8, filed on Feb. 1, 2008, 4 pages.
Response to Examination Report mailed Jun. 3, 2010, for European Patent Application No. 08714176.8, filed on Feb. 1, 2008, 9 pages.
Official Action for European Patent Application No. 08714176.8, dated Sep. 13, 2011 7 pages.
English translation of Official Action for Israel Patent Application No. 200176, dated Aug. 10, 2011 2 pages.
English Translation of Official Action for Israel Patent Application No. 200176, dated Jan. 29, 2013 2 pages.
English Translation of Official Action for Japan Patent Application No. 2009-548478, mailed Jan. 29, 2013 4 pages.
Official Action with English Translation for Taiwan Patent Application No. 096103983, dated Aug. 15, 2012 9 pages.
Official Action for U.S. Appl. No. 12/525,045, mailed Jan. 23, 2012 Restriction Requirement.
Official Action for U.S. Appl. No. 12/525,045, mailed Jun. 19, 2012 7 pages.
Official Action for U.S. Appl. No. 12/525,045, mailed Dec. 27, 2012 10 pages.
Notice of Acceptance for Australia Patent Application No. 2008214029, dated Jan. 21, 2014 2 pages.
Official Action for Canada Patent Application No. 2,676,783, dated Dec. 20, 2013 3 pages.
English Translation of Official Action for China Patent Application No. 200880010797.6, dated Nov. 19, 2013 4 pages.
Official Action with English Tranlation for Japan Patent Application No. 2009-548478, mailed Oct. 29, 2013 7 pages.
Official Action for Canada Patent Application No. 2,676,783, dated Apr. 8, 2015 3 pages.
Notice of Allowance for U.S. Appl. No. 12/525,045, mailed Apr. 21, 2015.
Official Action with English Translation for Taiwan Patent Application No. 096103983, dated May 29, 2015, 5 pages.
Notice of Allowance for Canada Patent Application No. 2,676,783, dated Oct. 9, 2015, 1 page.
Official Action with English Translation for Taiwan Patent Application No. 096103983, dated Nov. 17, 2015, 5 pages.

* cited by examiner

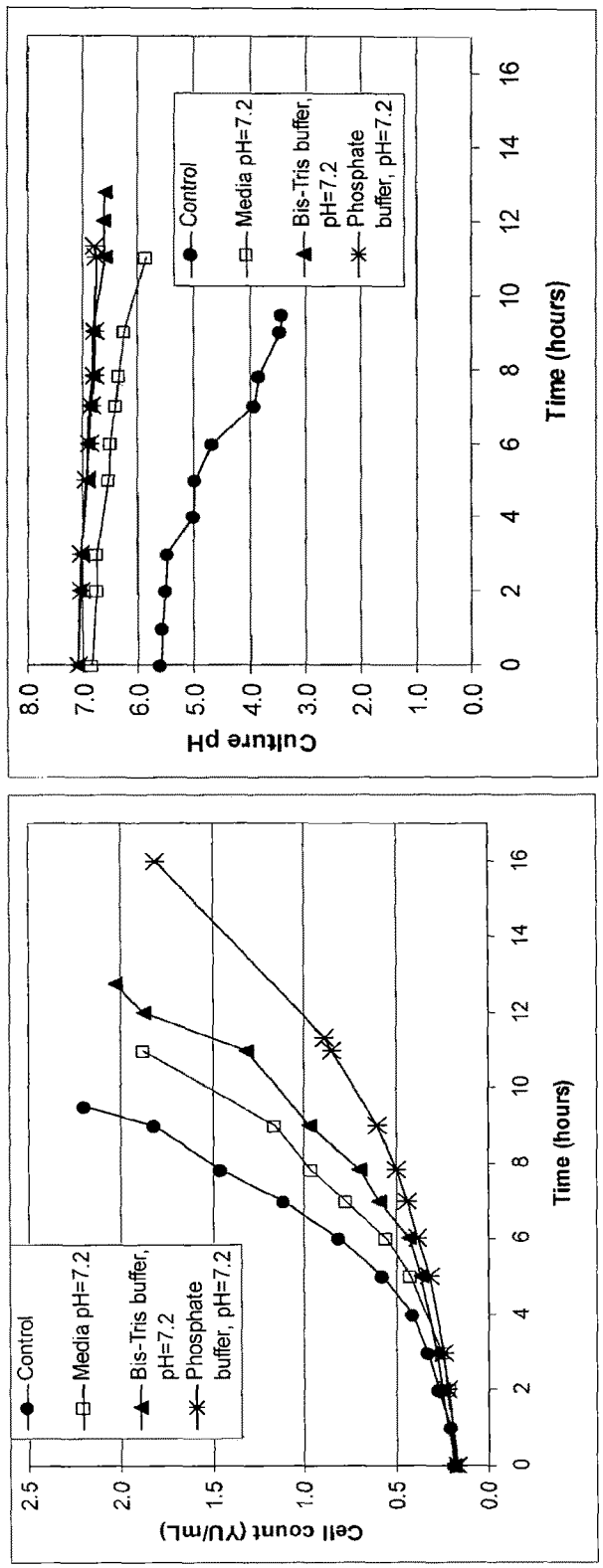
Figure 1 Effect of media pH on cell growth and culture pH

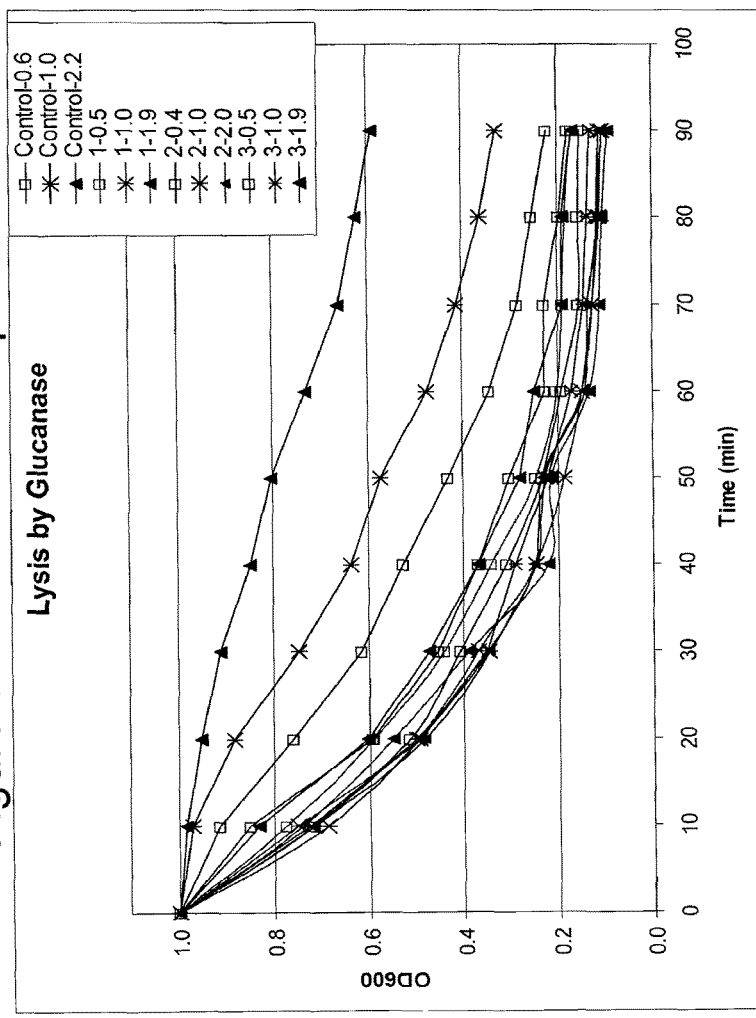
Figure 2 Effect of media pH on cell wall thickness
- Control culture (media pH~5.5) shows less efficient lysis as cell density increases.
- Flask1 = media pH 7.2, no buffer
- Flask 2 = media pH 7.2, Bis-Tris buffer
- Flask 3= media pH 7.2, phosphate buffer

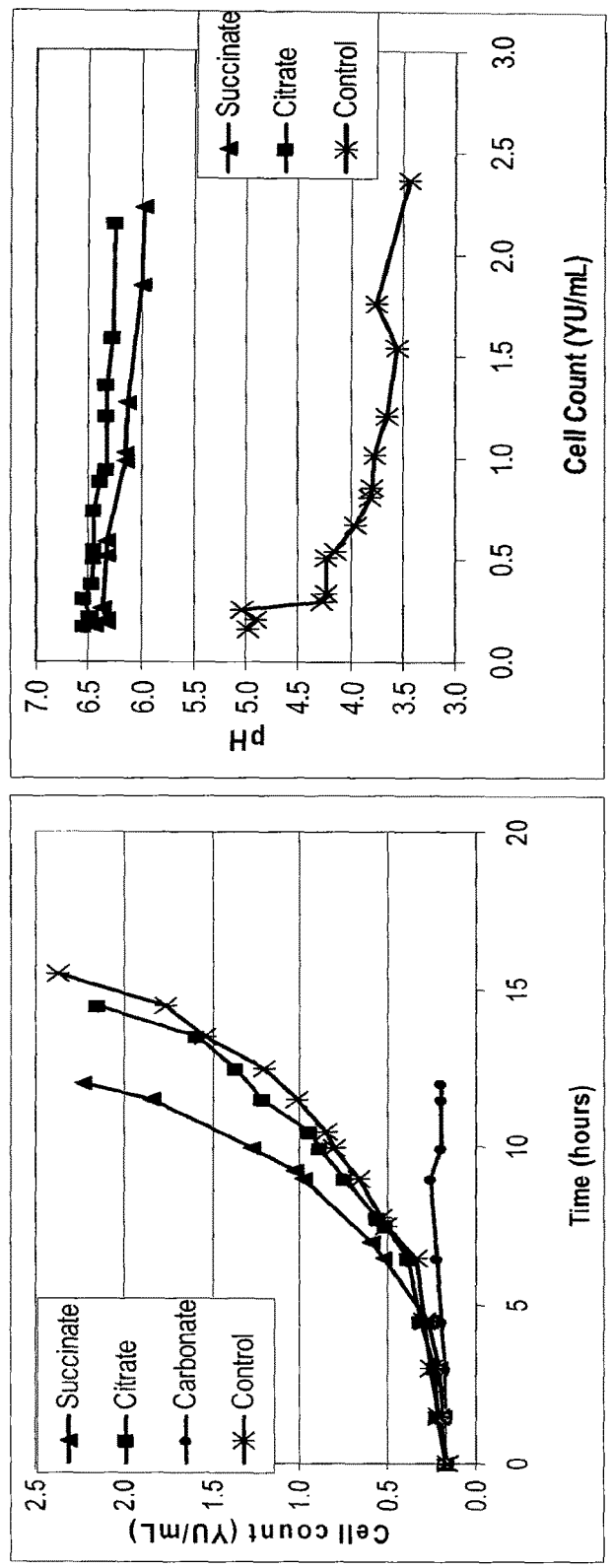
Figure 3 Testing different buffers (pH 6.5 media) Effects on cell growth and culture pH

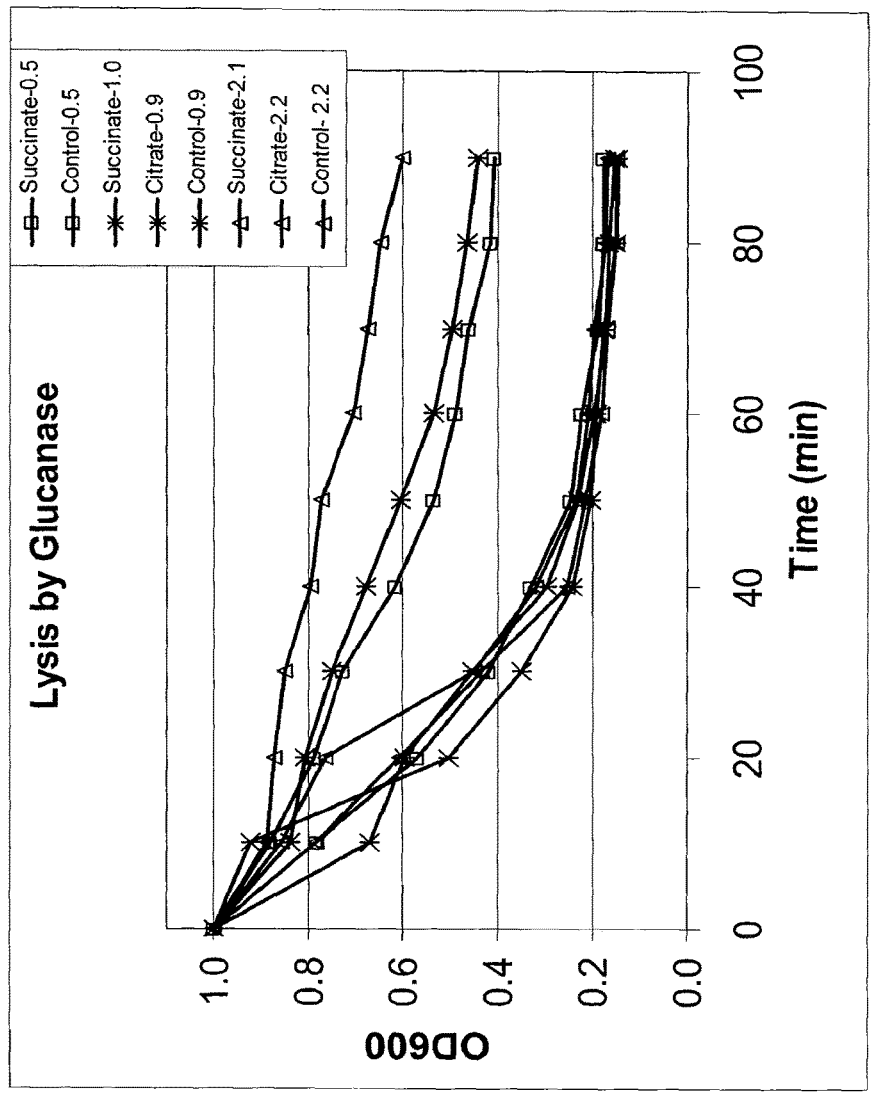
Figure 4 Testing new buffers (pH 6.5 media)

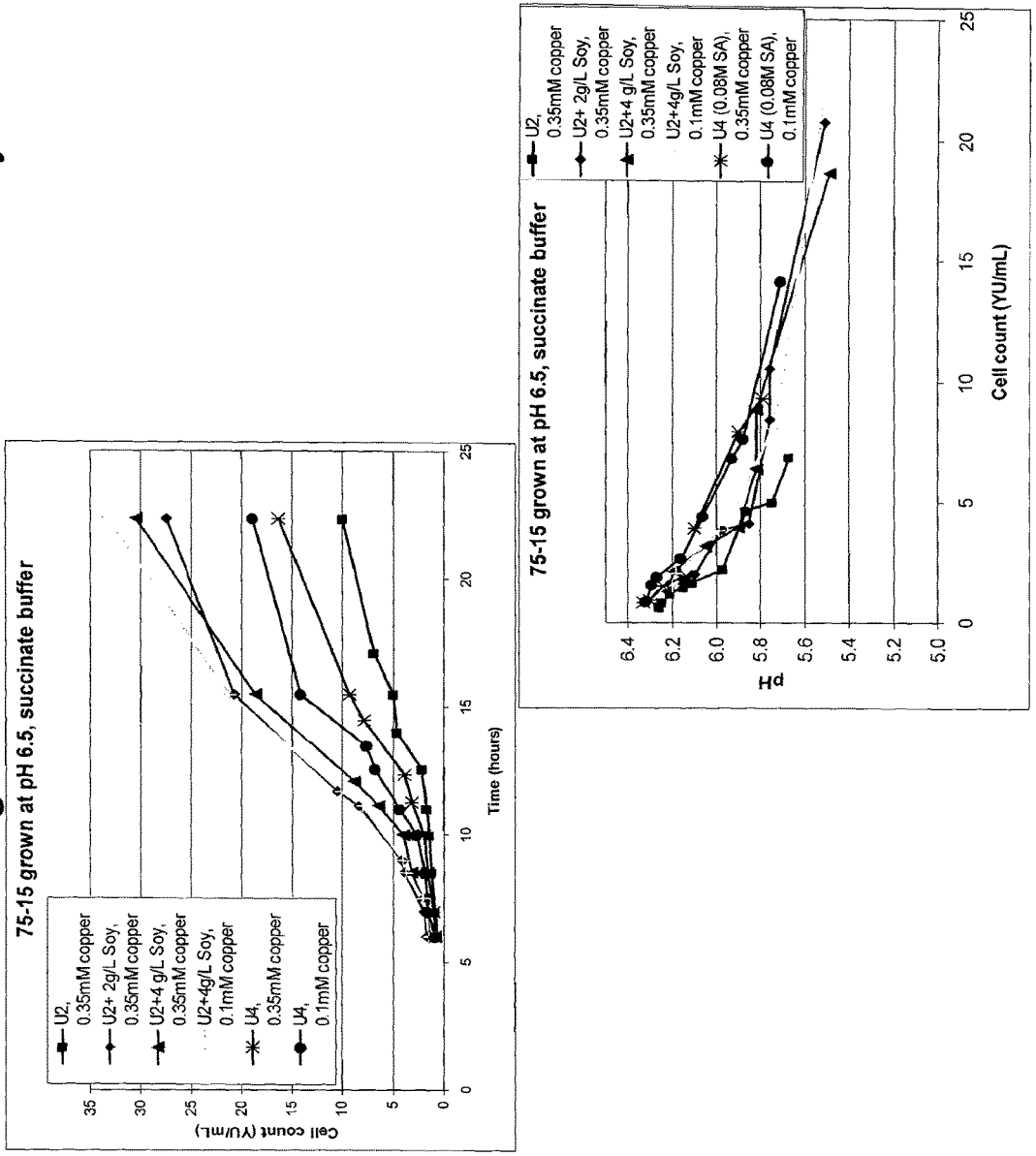
Figure 5 Media formulation study

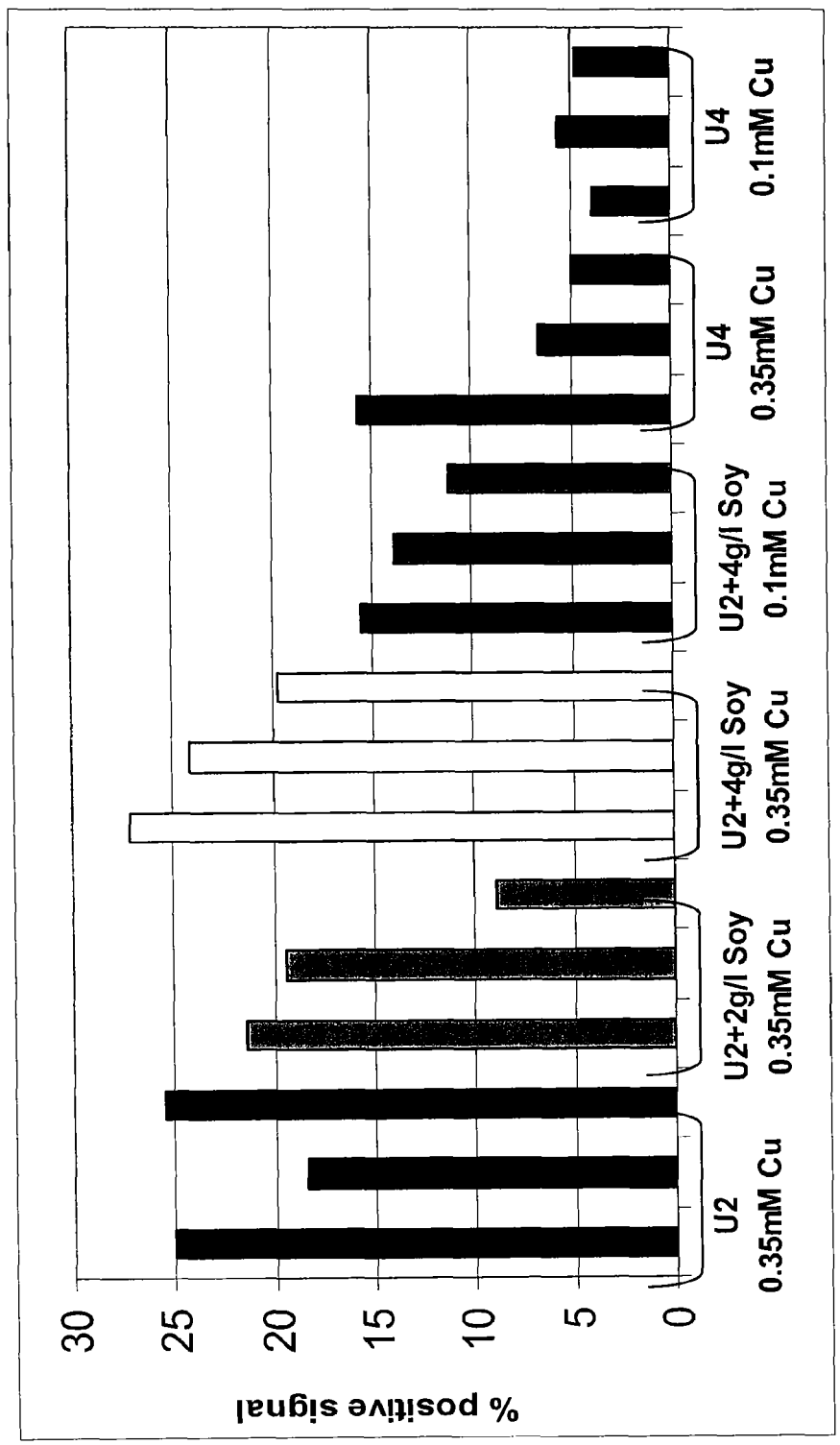

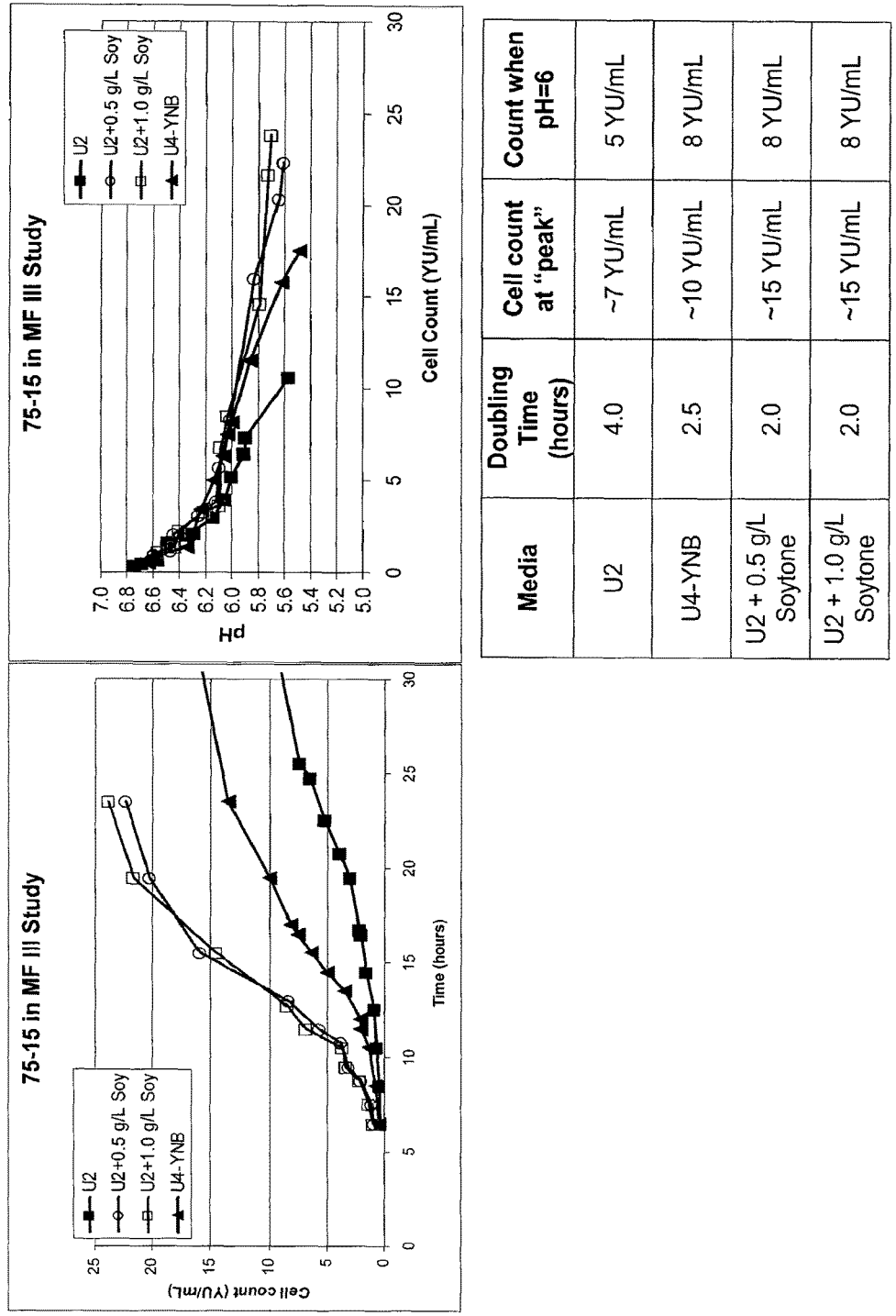
Figure 7 Media formulation study on cell growth and pH profiles

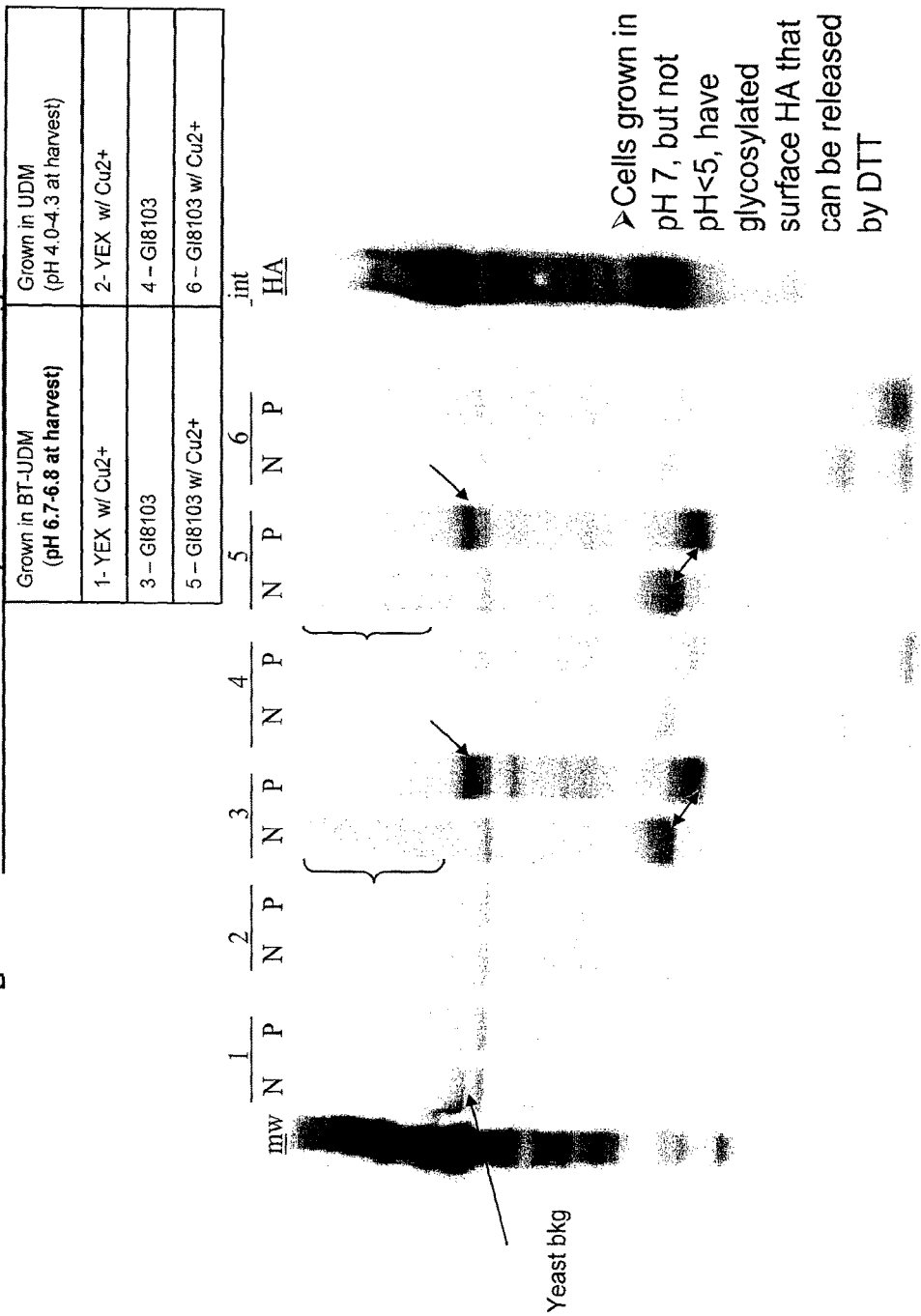
Figure 8 The effect of media pH levels on antigen

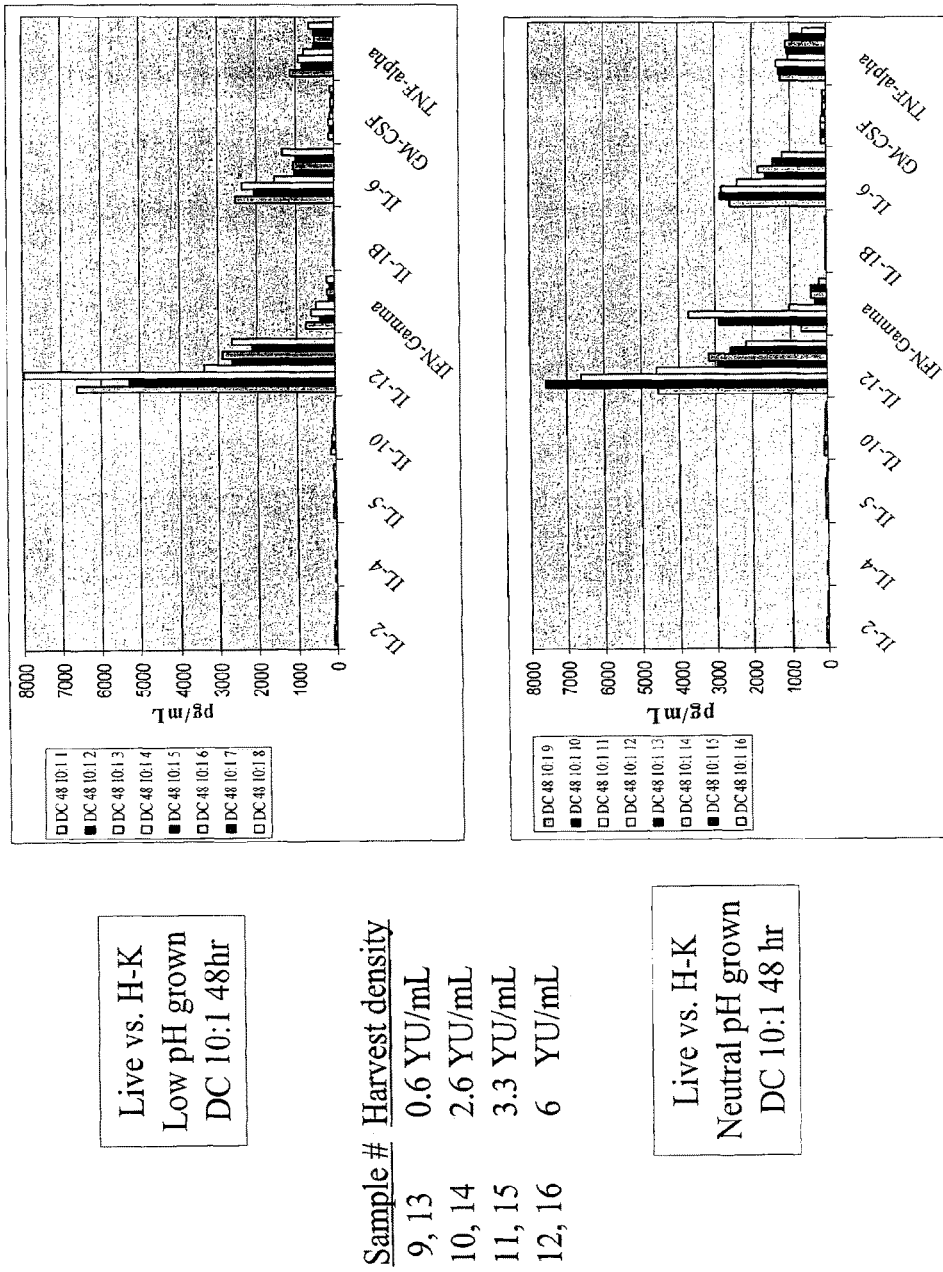
Figure 9 The effect of neutral pH on cytokine production

METHODS FOR PRODUCING YEAST-BASED VACCINES

RELATED APPLICATIONS

This patent application claims the benefit of priority under 35 U.S.C. §120 and is a continuation of U.S. patent application Ser. No. 12/525,045, filed Jan. 29, 2010, which is a national stage application under 35 U.S.C. §371 of PCT Application No. PCT/US2008/052843, filed Feb. 1, 2008, which claims the benefit of priority under 35 U.S.C. §119(e) of U.S. Provisional Patent Application No. 60/899,281, filed on Feb. 2, 2007. Each of U.S. patent application Ser. No. 12/525,045, PCT Application No. PCT/US2008/052843, and U.S. Provisional Patent Application No. 60/899,281 is hereby incorporated by reference in its entirety.

REFERENCE TO A SEQUENCE LISTING

This application contains a Sequence Listing submitted electronically as a text file by EFS-Web. The text file, named "3923-37-PCT_ST25", has a size in bytes of 8 KB, and was recorded on 15 Aug. 2012. The information contained in the text file is incorporated herein by reference in its entirety pursuant to 37 CFR §1.52(e)(5).

FIELD OF THE INVENTION

The invention relates to methods of growing yeast cultures at a neutral pH to improve yields and certain characteristics of yeast cultures. The method also relates to compositions produced by these methods.

BACKGROUND OF THE INVENTION

Vaccines are one of the most cost-effective measures available to the health care industry. There remains, however, an urgent need to develop safe and effective vaccines and adjuvants for a variety of diseases, including those due to infection by pathogenic agents, cancers, genetic defects and other disorders of the immune system. Publications on vaccine, for example, Rabinovich et al., *Science* 265, 1401-1404 (1994), state that there is still a need for safe and heat-stable vaccines that can be administered orally and that need to be administered only a few times, preferably early in life. Also preferred are combination vaccines that can protect individuals from more than one disease, as well as vaccines that do not require an adjuvant and that can elicit mucosal immunity. To date very few, if any, vaccines meet all of these criteria.

Subunit vaccines, the development of which was made possible by recombinant DNA technology, have been disappointing to date as they exhibit only limited immunogenicity. One example is the recent clinical testing of several HIV (human immunodeficiency virus) subunit vaccines which has been stopped due not only to limited efficacy of the vaccines but also because in some cases immunized individuals showed accelerated disease progression when they were subsequently exposed to HIV; see, for example, Cohen, *Science* 264:1839 (1994); and Cohen, *Science* 264: 660 (1994). One disadvantage of subunit vaccines, as well as of killed virus and recombinant live virus vaccines, is that while they appear to stimulate a strong humoral immune response, they fail to elicit protective cellular immunity. A major conclusion at the 1994 International AIDS Conference was that there remains a need for a cytotoxic T cell-mediated response to prevent, or reduce, HIV infectivity, which to date is lacking in vaccines in the clinic. In addition, HIV vaccines tested to date have failed to elicit immunity at the mucosal surfaces where primary HIV infection occurs.

Furthermore, the only adjuvants approved for use in the United States are the aluminum salts aluminum hydroxide and aluminum phosphate, neither of which stimulates cell-mediated immunity. In addition, aluminum salt formulations cannot be frozen or lyophilized, and such adjuvants are not effective with all antigens.

Yeast cells have been used in the production of subunit protein vaccines, including some of those tested in the aforementioned HIV vaccine trials. Yeast has also been fed to animals prior to immunization to try to prime the immune response in a non-specific manner (i.e., to stimulate phagocytosis as well as the production of complement and interferon). The results have been ambiguous, and such protocols have not generated protective cellular immunity; see, for example, Fattal-German et al., *Dev. Biol. Stand.* 77: 115-120 (1992) and Bizzini et al., *FEMS Microbiol. Immunol.* 2: 155-167 (1990).

In addition to vaccines, many gene and drug therapies require efficient and specific delivery vehicles to ensure the greatest possible benefit. Lack of an adequate delivery vehicle is a major roadblock to the application of gene therapy and significantly limits the therapeutic potential of many drugs. For example, recent reports have indicated that adenovirus vectors, which are currently being tested in the clinic for gene therapy applications, are stimulating undesirable immune and inflammatory responses and do not appear to be integrating in a desired manner; see, for example, Engelhardt et al., *Human Gene Therapy* 5: 1217-1229 (1994) and references cited therein.

Another major hurdle for yeast vaccine technology is the manufacturing process. Yeast cells have been cultured in the laboratories for many years and standard culture conditions have been established. See, for example, *Methods of Enzymology*, Vol. 194, Guthrie et al., eds., Cold Spring Harbor Laboratory Press (1990). Standard operating protocols generally involve culturing yeast in media that is acidic as measured by pH levels. However, culturing yeast in acidic media may result in the yeast exhibiting different biological properties that are not optimal for using yeast as antigen-bearing vehicles for purposes of immunomodulation or making vaccines. Thus, there is a need for methods for growing yeast such that the yeast exhibit properties that make them better suited for being antigen-bearing vehicles. The invention disclosed herein in based, in part, on the discovery that while yeast can grow in acidic media, the biological properties that the yeast exhibit when grown in acidic media is not as desirable as when yeast are grown in media that is at neutral pH levels.

The disclosure of all patents, patent applications, and publications cited herein are hereby incorporated by reference in their entirety for all purposes.

BRIEF SUMMARY OF THE INVENTION

The invention provides a method for growing yeast by culturing the yeast in medium wherein the media is maintained at a pH level of between 5.5 and 8 for at least 50% of time that the yeast are in culture. The invention also provides for a method for growing yeast by culturing the yeast in medium wherein the media is maintained at a pH level of between 5.5 and 8 and wherein the density of the yeast is at least 0.5 yeast units/mL.

In other aspect, the invention provides for growing yeast by culturing the yeast in medium with a pH level of at least 5.5. The invention also provides a method for growing yeast by culturing the yeast in medium wherein the media is maintained at a pH level of between 5.5 and 8. In an aspect of the invention, the yeast is *Saccharomyces cerevisiae*. In aspects of the invention the medium is buffered with succinate or succinic acid or the medium may additionally contain soytone. In other aspects of the invention, the yeast elicits an immune response. In other aspects of the invention, the yeast expresses an antigen, in some cases the antigen is a heterologous antigen. In some cases, the heterologous antigen is expressed on the surface of the yeast.

The invention provides for a composition comprising yeast cultured by any the methods and related aspects above.

The invention provides for a method for producing antigen-expressing yeast by culturing yeast containing an expression system for expressing the antigen in a medium wherein the pH of the media is at least 5.5. The invention also provides for a method for producing antigen-expressing yeast by culturing yeast containing an expression system for expressing the antigen wherein the media is maintained at a pH level of between 5.5 and 8. In one aspect, the yeast is *Saccharomyces cerevisiae*. In other aspects, the medium is buffered with succinate or succinic acid or the medium may additionally contain soytone. In other aspects of the invention, the yeast elicits an immune response. In other aspects of the invention, the yeast expresses an antigen, in some cases the antigen is a heterologous antigen. In some cases, the heterologous antigen is expressed on the surface of the yeast. In some aspects, the heterologous antigen is more readily accessible for interaction with other cells or agents than when the yeast is grown at a pH of less than 5.5.

The invention also provides for a composition comprising yeast cultured by the method disclosed above.

The invention also provides for a method of inducing a Th1-type response in an individual by administering to the individual a composition comprising antigen-expressing yeast wherein the yeast has been cultured in a medium with a pH level of at least 5.5.

The invention also provides for a method of inducing a Th1-type response in an individual by administering to the individual a composition comprising antigen-expressing yeast wherein the yeast has been cultured in media wherein the media is maintained at a pH level of between 5.5 and 8. In one aspect, the composition comprises dendritic cells loaded with yeast which have been cultured, maintained or harvested at a neutral pH. In another aspect, the yeast is *Saccharomyces cerevisiae*. In other aspects, the medium is buffered with succinate or succinic acid or the medium may additionally contain soytone. In other aspects of the invention, the yeast elicits an immune response. In other aspects of the invention, the yeast expresses an antigen, in some cases the antigen is a heterologous antigen. In some cases, the heterologous antigen is expressed on the surface of the yeast. In one aspect, the Th1-type response is interferon-gamma production. In another aspect, the Th1-type response is IL-12 production.

The invention also provides for a kit for culturing yeast comprising media wherein the pH of the media is at least 5.5 and instructions for the use of the media to culture yeast. The invention also provides for a kit for culturing yeast comprising media wherein the pH of the media is maintained at a pH level of between 5.5 and 8 and instructions for the use of the media to culture yeast. In other aspects, the medium is buffered with succinate or succinic acid or the medium may additionally contain soytone. In one aspect, the kit additionally includes yeast. In some cases, the yeast is frozen or lyophilized. In some cases, the yeast has been cultured in a media of at least pH 5.5 or has been cultured in a media wherein the pH of the media is maintained at a pH level of between 5.5 and 8. In other cases, the yeast is capable of replication.

BRIEF DESCRIPTION OF THE DRAWINGS

FIG. 1 depicts the effects of media pH levels on cell growth and also on the pH levels of the culture.

FIG. 2 depicts the effect of media pH levels on cell wall thickness.

FIG. 3 depicts the results from testing different buffers at a pH of about 6.5. The effects on the growth of 75-15 cells and the culture pH are shown.

FIG. 4 depicts the effect of various buffering agents on the cell wall thickness, as measured by lysis by glucanase. The culture media was buffered using either succinate or citrate to buffer the culture media to a pH level of about 6.5.

FIG. 5 depicts the results of a media formulation study wherein various additives were tested for its effect on growth and pH levels.

FIG. 6 depicts the results for yeast cell viability as part of a media formulation study. The surface expression of HA on yeast cell surface was measured using flow cytometry.

FIG. 7 depicts the results of a media formulation study on cell growth and pH profiles in which various additives were tested.

FIG. 8 depicts the results from an immunoblot assay of releasable hemagglutinin (HA) from intact yeast showing the difference in HA accessibility when yeast are grown at neutral versus when yeast are grown at lower pH conditions. The immunoblot is a western blot of DTT elutate from YEX and GI-8103.

FIG. 9 depicts the effect of culturing yeast cells at neutral and low pH levels on the secretion of cytokines by dendritic cells that have been loaded with yeast cells.

DETAILED DESCRIPTION OF THE INVENTION

The invention disclosed herein is based on the discovery that growing yeast at a neutral pH, at least pH 5.5, or between pH 5.5 and 8, or between pH 6 and 8, results in yeast with more desirable biological characteristics. Some of these desirable characteristics, which are detailed infra, include but are not limited to, ability to grow well at increased cell density, keeping yeast cell wall pliable and sensitive to digestion with cell wall digesting enzymes, and display of antigens in a manner that makes them more accessible to other cells and/or agents.

General Techniques

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Pro-* tein Synthesis, and Energetics, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russell, 2001), (jointly referred to herein as "Sambrook"); *Current Protocols in Molecular Biology* (F. M. Ausubel et al., eds., 1987, including supplements through 2001); *PCR: The Polymerase Chain Reaction*, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual Cold Spring Harbor Laboratory Press*, Cold Spring Harbor, N.Y. (jointly referred to herein as "Harlow and Lane"), Beaucage et al. eds., *Current Protocols in Nucleic Acid Chemistry* John Wiley & Sons, Inc., New York, 2000) and *Vaccines*, S. Plotkin and W. Orenstein, eds., $3^{rd}$ edition (1999).

Definitions

As used herein, the general use of the term "neutral pH" refers to a pH level of at least 5.5. The neutral pH range can be between about pH 5.5 and about pH 8, preferably between about pH 6 and about 8. One of skill the art will appreciate that minor fluctuations (e.g., tenths or hundredths) can occur when measuring with a pH meter and, as such, should take this into account when determining the pH level at any given time.

As used herein, the general use of the term "antigen" refers any molecule that can be recognized by the adaptive immune system. In one aspect, an antigen is a molecule that binds specifically to an antibody. The molecule can be any portion of a protein (peptide, partial protein, full-length protein) wherein the protein is naturally occurring or synthetically derived, or part of a cellular composition (whole cell, cell lysate or disrupted cells), part of an organism (whole organism, lysate or disrupted cells) or a carbohydrate or a portion thereof. The antigen can elicit an antigen-specific humoral immune response by itself or with the use of another compound such as an adjuvant (like crushed yeast cells). In another aspect, an antigen is recognized by T lymphocytes (or T cells) in the context of major histocompatibility complexes (MHCs). In another aspect, the antigen can act as a toleragen, against the same or similar antigens that are encountered within the cells and tissues of the animal to which the antigen is administered.

In one aspect of the present invention, when referring to the stimulation of an immune response, the "antigen" can be an "immunogen" Immunogens are molecules which can elicit an adaptive immune response, e.g., induction of antibody production. The immunogen can in some cases generate memory cells that will produce antibodies which recognize the antigen upon future exposure to the antigen. As is well-known to all persons of skill in this field, immunogens can also be recognized by T lymphocytes, although the form of the immunogen recognized by T lymphocytes will be different from the form of the immunogen that the antibody recognizes.

Methods of Culturing Yeast

The invention provides for methods for culturing yeast that produces desirable characteristics, such as high expression of a desired antigen, cell wall pliability, and display of antigen.

These methods are broadly applicable to all yeast. Yeast are unicellular microorganisms that belong to one of three classes: Ascomycetes, Basidiomycetes and Fungi Imperfecti. While pathogenic yeast strains, or nonpathogenic mutants thereof can be used in accordance with the present invention, in one aspect, nonpathogenic yeast strains are used. Examples of nonpathogenic yeast strains include *Saccharomyces, Candida, Cryptococcus, Hansenula, Kluyveromyces, Pichia, Rhodotorula, Schizosaccharomyces* and *Yarrowia*. In one aspect, *Saccharomyces, Candida, Hansenula, Pichia* and *Schizosaccharomyces* are used. In yet other aspects, *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica* are used. It is understood the invention is not limited to the species list above and that one of skill in the art can apply the teachings here in any type of yeast. In another aspect, *Saccharomyces cerevisiae* (*S. cerevisiae*) is used to practice the methods of the invention. *S. cerevisiae* is preferred due to it ease for molecular manipulation and being "Generally Recognized As Safe" or "GRAS" for use as food additives (GRAS, FDA proposed Rule 62FR18938, Apr. 17, 1997).

The pH level is important in the culturing of yeast. One of skill in the art will appreciate that the culturing process includes not only the start of the yeast culture but the maintenance of the culture as well. The yeast culture may be started at any pH level, however, since the media of a yeast culture tends to become more acidic (i.e., lowering the pH) over time, care must be taken to monitor the pH level during the culturing process.

In some aspects of the invention, the yeast is grown in a media at a pH level of at least 5.5. In other aspects, the yeast is grown at a pH level of about 5.5. In other aspects, the yeast is grown at a pH level of between 5.5 and 8. In some cases, the yeast culture is maintained at a pH level of between 5.5 and 8. In other aspects, the yeast is grown at a pH level of between 6 and 8. In some cases, the yeast culture is maintained at a pH level of between 6 and 8. In other aspects, the yeast is grown and/or maintained at a pH level of between 6.1 and 8.1. In other aspects, the yeast is grown and/or maintained at a pH level of between 6.2 and 8.2. In other aspects, the yeast is grown and/or maintained at a pH level of between 6.3 and 8.3. In other aspects, the yeast is grown and/or maintained at a pH level of between 6.4 and 8.4. In other aspects, the yeast is grown and/or maintained at a pH level of between 5.5 and 8.5. In other aspects, the yeast is grown and/or maintained at a pH level of between 6.5 and 8.5. In other aspects, the yeast is grown at a pH level of about 5.6, 5.7, 5.8 or 5.9. In another aspect, the yeast is grown at a pH level of about 6. In another aspect, the yeast is grown at a pH level of about 6.5. In other aspects, the yeast is grown at a pH level of about 6, 6.1, 6.2, 6.3, 6.4, 6.5, 6.6, 6.7, 6.8, 6.9 or 7.0. In other aspects, the yeast is grown at a pH level of about 7, 7.1, 7.2, 7.3, 7.4, 7.5, 7.6, 7.7, 7.8, 7.9, or 8.0. In other aspects, the yeast is grown at a level of above 8.

In one aspect, yeast is cultured such that the pH level of the medium does not drop below pH 5.5. In some cases, the drop below pH 5.5 is not more than 5 minutes. In other cases, the drop below pH 5.5 is not more than 10 minutes, preferably 20, 30, 40, 50 or 60 minutes. In other cases, the drop below pH 5.5 is not more than 1 hour. In another aspect, yeast is cultured such that the pH level of the medium does not drop below 5.0. In some cases, the drop below pH 5.0 is not more than 5 minutes. In other cases, the drop below pH 5.0 is not more than 10 minutes, preferably 20, 30, 40, 50 or 60 minutes. In other cases, the drop below pH 5.0 is not more than 1 hour. As such, the longer time the yeast are grown in a medium that is at least pH 5.5 or above, the better the results will be in terms of obtaining yeast with desirable characteristics described infra.

In one aspect, the use of neutral pH methods to grow yeast cells means that the yeast cells are grown in neutral pH for at least 50% of the time that the yeast are in culture. It is more preferable that the yeast are grown at neutral pH for at least 60% of the time they are in culture, more preferably at least 70% of the time they are in culture, more preferably at least 80% of the time they are in culture, and most preferably at least 90% of the time they are in culture.

In another aspect, growing yeast at neutral pH includes culturing yeast cells for at least five minutes at neutral pH, preferably at least 15 minutes at neutral pH, more preferably at least one hour at neutral pH, more preferably at least two hours, even more preferably, at least three hours or longer.

As noted earlier, as yeast grow and replicate, the cell densities become greater and the acidity level in the culture media rises. As such, it is recommended that as the yeast are cultured at a pH level of at least 5.5 and/or maintained at at least pH 5.5 as the yeast density increases. In one aspect, the yeast are grown and/or maintained between a pH of 5.5 and 8 as the yeast density is 0.5 yeast units (YU)/ml or above. In other aspects, the yeast are grown and/or maintained between a pH of 5.5 and 8 when the yeast density is at least 0.6 YU/ml or above, preferably 0.7 YU/ml or above, 0.8 YU/ml or above, 0.9 YU/ml or above, or 1 YU/ml or above.

In another aspect, the yeast are grown and/or maintained between a pH of 6 and 8 as the yeast density is 0.5 YU/ml or above. In other aspects, the yeast are grown and/or maintained between a pH of 6 and 8 when the yeast density is at least 0.6 YU/ml or above, preferably 0.7 YU/ml or above, 0.8 YU/ml or above, 0.9 YU/ml or above, or 1 YU/ml or above.

In some aspects, it is preferable at the time of harvest that the yeast culture is at a neutral pH level. In some cases, the yeast culture, at the time of harvest, will be at a pH level of between 6 and 8. In other cases, the yeast culture, at the time of harvest, will be at a pH level of between 5.5 and 8.

The culture media can be brought to a pH level of at least 5.5 by any means. In one aspect, succinic acid (and any related forms, e.g., the anion succinate) is used for buffering the culture media. As further detailed in the Examples, the use of succinate to buffer the culture media to at least pH 5.5 allows for yeast to have a doubling time of about two to two and a half hours. Succinate is available from commercially available sources (e.g., Sigma Chemicals). In other aspects, citrate may be used to bring the media to a pH of at least 5.5. One of skill in the art will be able to readily determine other buffering agents which may be used to bring the media to a pH of at least 5.5 while keeping the yeast viable. The concept of buffering agents to keep a solution at a steady pH level is well-known in the art and as such, will not be discussed in detail herein. If yeast grown according to the invention are being used for pharmaceutical formulations (e.g., vaccines), it is recommended that GMP grade material be used.

In addition, other supplements may be added to the culture media to improve the media. Other supplements which are particularly helpful to add to the culture media include soytone. Soytone is readily available from commercial sources (e.g., BD Difco). As shown in the Examples and figures, the addition of soytone to the culture media supports higher density for growth at neutral pH. Furthermore, the addition of soytone supports expression of an antigen of interest, hemagglutinin (HA) of the influenza virus.

Other additives may be added to the yeast culture for other purposes, such as inducing expression of heterologous genes. In some aspects, copper is used to induce the expression of hemagglutinin expression. However, the use of copper is not ideal at neutral pH thus, for control of inducible genes to be expressed in yeast grown at neutral pH; an additive other than copper would be recommended.

Effects of Neutral pH on Yeast Culture

The use of a neutral pH in culturing yeast promotes several biological effects that are desirable characteristics for using the yeast as vehicles for immunomodulation and/or eliciting immune responses. In one aspect, culturing the yeast in neutral pH allows for good growth of the yeast without any negative effect on the doubling time (e.g., slowing down the doubling time). The yeast can continue to grow to high densities without losing their cell wall pliability.

In another aspect, the use of a neutral pH, such as a pH of at least 5.5 or between pH 5.5 and 8, allows for the production of yeast with pliable cell walls and/or yeast that have a sensitivity to cell wall digesting enzymes (e.g., glucanase) at all harvest densities. As such, the invention provides for methods and compositions of yeast with cell wall pliability as measured by traditional assays (e.g., sensitivity to glucanase). Prior experiments had established that yeast lost its sensitivity to digestion with cell wall digesting enzymes at harvest densities of about 0.5 YU (yeast units)/ml. As such, one advantage is that comparisons done with yeast cultured in standard growth media at 0.5 YU/ml can be used for comparison with neutral pH growth at any density. This trait is desirable because yeast with flexible cell walls can exhibit unique immune responses, such as promoting the secretion of cytokines (e.g., INF-gamma) in the cells hosting the yeast. Another reason why one of skill in the art would use the neutral pH methodology is that it allows for greater accessibility to the antigens located in the cell wall. This is useful for greater immunogenicity and also for antibody detection of expressed protein, measured by standard techniques such as flow cytometry.

Yet another desirable characteristic that is observed in yeast cultured at neutral pH is the expression of antigens in a way that is beneficial for purposes of immunomodulation. In one aspect, the yeast are used as vehicles for antigen expression (see, for example, U.S. Pat. Nos. 5,830,463 and 7,083,787). The antigen may be an antigen native to yeast or alternatively, a heterologous antigen that is expressed by the yeast. In some aspects, the use of yeast for expression of antigens is helpful for development of vaccines, prophylactics, and therapeutics to combat various diseases and ailments (e.g., infectious diseases or cancer). Using neutral pH methodology, one of skill in the art can produce antigen-bearing yeast wherein the antigen is more accessible to other cells (e.g., for immune co-stimulatory functions or immune regulation) or to other agents (e.g., antibodies for detection). In addition, the use of neutral pH for some antigens, such as the influenza HA antigen, allows for release of the di-sulfide bonded HA by treatment with dithiothreitol (DTT) that is not possible when the HA-expressing yeast is cultured in media where the pH drops below pH 5. In some cases, this occurs when the pH drops below pH 5 for any length of time. In other cases, this occurs when the pH drops below pH 5 for one or a few minutes or one or more hours.

Another desirable characteristic that yeast cultured following the neutral pH methodologies exhibit is the secretion of Th1-type cytokines from cells that have been exposed to the yeast. Examples of Th1-type cytokines include, but are not limited to, interferon-gamma, IL-12, and IL-2. As further detailed in the Examples, dendritic cells that were loaded with yeast that had been grown following neutral pH protocols exhibit increased levels of interferon-gamma secretion and expression as compared to yeast grown at low (acidic) pH media. There was no reduction in the levels of IL-12 secretion when using the neutral pH culturing methods. As such, one of skill in the art can use the neutral pH methodologies disclosed herein for immunomodulation purposes, e.g., inducing a Th1-type response in an individual that is afflicted with a disease or disorder that would benefit from an enhanced Th1-type response.

Compositions of Yeast Grown Using Neutral pH Methodology

The invention also contemplates compositions comprising yeast which are grown using the neutral pH methodologies disclosed herein. In one aspect, the composition comprises yeast that express native antigens, either on its surface or internally or both. This composition can be useful for various purposes, such as administration as an adjuvant. In another aspect, the composition comprises yeast that express heterologous antigens, either on its surface or internally or both. This composition can be useful for various purposes, such as immunomodulation in an individual in need thereof and the development of vaccines.

These compositions can also include pharmaceutically acceptable excipients and/or carriers. Pharmaceutically acceptable carriers may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. The formulation of compositions comprising yeast grown under neutral pH conditions with a pharmaceutically acceptable excipient is generally routine for one of skill in the art.

Kits of the Invention

The invention contemplates kits comprising media components for culturing yeast under neutral pH conditions. In one aspect, the kit includes media components containing succinate or succinic acid which can be used to bring the media to a pH of at least 5.5 and a set of instructions for its use. In another aspect, the kit further includes soytone as an additional component. In another aspect, the kit further includes yeast cells. The yeast cells can be frozen for starting a culture using the protocols disclosed herein. In another aspect, the yeast cells can have already been cultured by the methods disclosed herein prior to being frozen for packaging as part of the kit. In another aspect, the yeast cells can be lyophilized and optionally be included in the kit. In another aspect, the kit comprises yeast prepared according to the methods disclosed herein that is capable of replication.

The following examples are provided to illustrate certain aspects of the invention. They are not intended to limit the invention in any manner.

EXAMPLES

Example 1

Yeast Media Formulations

Various types of media can be used to culture yeast and be adjusted such that the pH level is neutral. Several examples of media which can be used are given below, however, it is to be understood that the invention is not limited to the use of these media components or media protocols.

One standard media recipe is ULDM media which is as follows:

| Component | g/L | 20 L | Source |
| --- | --- | --- | --- |
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.02 | 0.4 | JTBaker 2092 |
| Histidine | 0.02 | 0.4 | JTBaker N327 |
| Glucose monohydrate | 25.0 | 500.0 | EMD 1.08342.2500 |

Another standard media recipe is UL2 media which is as follows:

| Component | g/L | 20 L | Source |
| --- | --- | --- | --- |
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.4 | 0.8 | Sigma A9795 |
| Tryptophan | 0.4 | 0.8 | JTBaker 2092 |
| Histidine | 0.4 | 0.8 | JTBaker N327 |
| Glucose monohydrate | 15.0 | 300.0 | EMD 1.08342.2500 |

Another standard media recipe is UL3 media which is as follows:

| Component | g/L | 20 L | Source |
| --- | --- | --- | --- |
| YNB w/o ammonium sulfate and amino acids | 2.5 | 50.0 | Difco 233520 |
| Ammonium sulfate OR | 7.5 | 150.0 | EMD AX13853 |
| YNB w/o amino acids | 10.0 | 200.0 | Difco |
| Adenine | 0.06 | 1.2 | Sigma A9795 |
| Tryptophan | 0.06 | 1.2 | JTBaker 2092 |
| Histidine | 0.06 | 1.2 | JTBaker N327 |
| Glucose monohydrate | 22.5 | 450.0 | EMD 1.08342.2500 |

Another standard media recipe is UL4 media which is as follows:

| Component | g/L | 20 L | Source |
| --- | --- | --- | --- |
| YNB w/o ammonium sulfate and amino acids | 3.4 | 68.0 | Difco 233520 |
| Ammonium sulfate OR | 10.0 | 200.0 | EMD AX13853 |
| YNB w/o amino acids | 13.4 | 268.0 | Difco |
| Adenine | 0.08 | 1.6 | Sigma A9795 |
| Tryptophan | 0.08 | 1.6 | JTBaker 2092 |
| Histidine | 0.08 | 1.6 | JTBaker N327 |
| Glucose monohydrate | 30.0 | 600.0 | EMD 1.08342.2500 |

Another standard media recipe is UDM media which is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.02 | 0.4 | JTBaker 2092 |
| Histidine | 0.02 | 0.4 | JTBaker N327 |
| Leucine | 0.03 | 0.6 | JTBaker 2083 |
| Glucose monohydrate | 25.0 | 500.0 | EMD 1.08342.2500 |

Another standard media recipe is U2 media which is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.04 | 0.8 | Sigma A9795 |
| Tryptophan | 0.04 | 0.8 | JTBaker 2092 |
| Histidine | 0.04 | 0.8 | JTBaker N327 |
| Leucine | 0.06 | 1.2 | JTBaker 2083 |
| Glucose monohydrate | 15.0 | 300.0 | EMD 1.08342.2500 |

Another standard media recipe is U3 media which is as follows:

| Component | g/L | 20 L | Source |
|---|---|---|---|
| YNB w/o ammonium sulfate and amino acids | 2.5 | 50.0 | Difco 233520 |
| Ammonium sulfate OR | 7.5 | 150.0 | EMD AX13853 |
| YNB w/o amino acids | 10.0 | 200.0 | Difco |
| Adenine | 0.06 | 1.2 | Sigma A9795 |
| Tryptophan | 0.06 | 1.2 | JTBaker 2092 |
| Histidine | 0.06 | 1.2 | JTBaker N327 |
| Leucine | 0.09 | 1.8 | JTBaker 2083 |
| Glucose monohydrate | 22.5 | 450.0 | EMD 1.08342.2500 |

Another standard media recipe is U4 media which is as follows:

| Component | g/L | 20 L | Source |
|---|---|---|---|
| YNB w/o ammonium sulfate and amino acids | 3.4 | 68.0 | Difco 233520 |
| Ammonium sulfate OR | 10.0 | 200.0 | EMD AX13853 |
| YNB w/o amino acids | 13.4 | 268.0 | Difco |
| Adenine | 0.08 | 1.6 | Sigma A9795 |
| Tryptophan | 0.08 | 1.6 | JTBaker 2092 |
| Histidine | 0.08 | 1.6 | JTBaker N327 |
| Leucine | 0.12 | 2.4 | JTBaker 2083 |
| Glucose monohydrate | 30.0 | 600.0 | EMD 1.08342.2500 |

Standard media formulations may be supplemented with additional amino acids. The following protocols are exemplary media formulations.

The ULDMaa media formulation is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.04 | 0.8 | JTBaker 2092 |
| Histidine | 0.04 | 0.8 | JTBaker N327 |
| Glucose monohydrate | 25.0 | 500.0 | EMD 1.08342.2500 |

The UL2aa media formulation is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.04 | 0.8 | Sigma A9795 |
| Tryptophan | 0.06 | 1.2 | JTBaker 2092 |
| Histidine | 0.06 | 1.2 | JTBaker N327 |
| Glucose monohydrate | 15.0 | 300.0 | EMD 1.08342.2500 |

The UL3aa media formulation is as follows:

| Component | g/L | 20 L | Source |
|---|---|---|---|
| YNB w/o ammonium sulfate and amino acids | 2.5 | 50.0 | Difco 233520 |
| Ammonium sulfate OR | 7.5 | 150.0 | EMD AX13853 |
| YNB w/o amino acids | 10.0 | 200.0 | Difco |
| Adenine | 0.06 | 1.2 | Sigma A9795 |
| Tryptophan | 0.08 | 1.6 | JTBaker 2092 |
| Histidine | 0.08 | 1.6 | JTBaker N327 |
| Glucose monohydrate | 22.5 | 450.0 | EMD 1.08342.2500 |

The UDMaa media formulation is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.04 | 0.8 | JTBaker 2092 |
| Histidine | 0.04 | 0.8 | JTBaker N327 |
| Leucine | 0.06 | 1.2 | JTBaker 2083 |
| Glucose monohydrate | 25.0 | 500.0 | EMD 1.08342.2500 |

The U2aa media formulation is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |

-continued

| Component | g/L | 20 L | Source |
|---|---|---|---|
| Adenine | 0.04 | 0.8 | Sigma A9795 |
| Tryptophan | 0.06 | 1.2 | JTBaker 2092 |
| Histidine | 0.06 | 1.2 | JTBaker N327 |
| Leucine | 0.09 | 1.8 | JTBaker 2083 |
| Glucose monohydrate | 15.0 | 300.0 | EMD 1.08342.2500 |

The U3aa media formulation is as follows:

| Component | g/L | 20 L | Source |
|---|---|---|---|
| YNB w/o ammonium sulfate and amino acids | 2.5 | 50.0 | Difco 233520 |
| Ammonium sulfate OR | 7.5 | 150.0 | EMD AX13853 |
| YNB w/o amino acids | 10.0 | 200.0 | Difco |
| Adenine | 0.06 | 1.2 | Sigma A9795 |
| Tryptophan | 0.08 | 1.6 | JTBaker 2092 |
| Histidine | 0.08 | 1.6 | JTBaker N327 |
| Leucine | 0.12 | 2.4 | JTBaker 2083 |
| Glucose monohydrate | 22.5 | 450.0 | EMD 1.08342.2500 |

In another aspect, succinate-containing buffered media is used. Examples of succinate-containing yeast media are below. The UDMS media formulation, adjusted to pH 6.9 is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.02 | 0.4 | Sigma A9795 |
| Tryptophan | 0.02 | 0.4 | JTBaker 2092 |
| Histidine | 0.02 | 0.4 | JTBaker N327 |
| Leucine | 0.03 | 0.6 | JTBaker 2083 |
| Glucose monohydrate | 25.0 | 500.0 | EMD 1.08342.2500 |
| Succinic acid | 9.45 | 189.0 | EMD SX 1040-3 |

The U2S media formulation, adjusted to pH 6.9 is as follows:

| Component | g/L | 20 L | Source |
|---|---|---|---|
| YNB w/o ammonium sulfate and amino acids | 1.7 | 34.0 | Difco 233520 |
| Ammonium sulfate OR | 5.0 | 100.0 | EMD AX13853 |
| YNB w/o amino acids | 6.7 | 134.0 | Difco |
| Adenine | 0.04 | 0.8 | Sigma A9795 |
| Tryptophan | 0.04 | 0.8 | JTBaker 2092 |
| Histidine | 0.04 | 0.8 | JTBaker N327 |
| Leucine | 0.06 | 1.2 | JTBaker 2083 |
| Glucose monohydrate | 15.0 | 300.0 | EMD 1.08342.2500 |
| Succinic acid | 9.45 | 189.0 | EMD SX 1040-3 |

The U3S media formulation, adjusted to pH 6.9 is as follows:

| Component | g/L | 20 L | Source |
|---|---|---|---|
| YNB w/o ammonium sulfate and amino acids | 2.5 | 50.0 | Difco 233520 |
| Ammonium sulfate OR | 7.5 | 150.0 | EMD AX13853 |
| YNB w/o amino acids | 10.0 | 200.0 | Difco |
| Adenine | 0.06 | 1.2 | Sigma A9795 |
| Tryptophan | 0.06 | 1.2 | JTBaker 2092 |
| Histidine | 0.06 | 1.2 | JTBaker N327 |
| Leucine | 0.09 | 1.8 | JTBaker 2083 |
| Glucose monohydrate | 22.5 | 450.0 | EMD 1.08342.2500 |
| Succinic acid | 9.45 | 189.0 | EMD SX 1040-3 |

The U4S media formulation, adjusted to pH 6.9 is as follows:

| Component | g/L | 20 L | Source |
|---|---|---|---|
| YNB w/o ammonium sulfate and amino acids | 3.4 | 68.0 | Difco 233520 |
| Ammonium sulfate OR | 10.0 | 200.0 | EMD AX13853 |
| YNB w/o amino acids | 13.4 | 268.0 | Difco |
| Adenine | 0.08 | 1.6 | Sigma A9795 |
| Tryptophan | 0.08 | 1.6 | JTBaker 2092 |
| Histidine | 0.08 | 1.6 | JTBaker N327 |
| Leucine | 0.12 | 2.4 | JTBaker 2083 |
| Glucose monohydrate | 30.0 | 600.0 | EMD 1.08342.2500 |
| Succinic acid | 9.45 | 189.0 | EMD SX 1040-3 |

Example 2

Effect of Media pH on Cell Growth and Culture pH

The effect of media pH on cell growth and culture pH were tested, as shown in FIG. 1. Cells were grown in U2 media supplemented with Bis-Tris buffer, pH 7.2 or phosphate buffer, pH 7.2. Control cultures were gown in U2 media without buffer added to the media. For conditions marked as control (same as media pH 5.5) or media pH 7.2, the growth media for these controls was either adjusted to pH 5.5 or pH 7.2 with base (NaOH) prior to inoculating with the yeast. The cultures were incubated at 30° C. and monitored for cell count and culture pH for up to 16 hours. The results indicate that buffers at varying pH levels affected growth rates of the yeast. As shown in FIG. 1, the doubling times ranged from 2.8 to 4.5 hours. The pH in unbuffered pH 7 media was ~5.5 at 2.0 YU/mL, which indicates the need for some form of buffering agent to keep the pH at a neutral level.

Example 3

Effect of Media pH on Cell Wall Thickness

The effect of media pH was tested to determine if it had any effect on cell wall thickness. Growth media and conditions were the same as in Example 1. Cultures were harvested at densities ranging from 0.5 to 2.0 YU/mL. In the legend for FIG. 2, the density when the cultures were harvested is listed as the number following the dash mark, e.g. control-0.6 means cells grown in unbuffered media at pH 5.5, then harvested when cells reached 0.6 YU/mL density. The conditions for flasks 1-3 (e.g. 1-0.5, 2-2.0 or 3-1.0) are listed below the figure and the cell density at harvest is marked in the legend. The lysis assay protocol used was as follows: (1) re-suspend 10YU of washed cells in 1 mL of Tris-BME; (2) pull a "Time 0" sample and measure the OD at 600 nm; (3) add 20 U of glucanase; (4) rotate at 30° C.; (5) every 10 minutes, take a sample and measure the OD.

As can be observed in FIG. 2, the control culture (media pH~5.5) shows less efficient lysis as cell density increases. Flask 2 shows the effect of media at pH 7.2 with no buffer. Flask 2 shows the effect of media at pH 7.2 with Bis-Tris buffer. Flask 3 shows the effect of media at pH 7.2 with phosphate buffer.

Thus, the results indicate that growing yeast buffered at about pH 5.5 or higher keeps the cell wall pliable and sensitive to digestion with cell wall digesting enzymes (e.g., making spheroplasts with lyticase/glucanase) at all harvest densities. In contrast, with the standard process commonly used in many yeast laboratories, the sensitivity was lost at harvest densities >0.5 YU/mL. For ease of comparison, 0.5 YU/mL with standard growth media is often used for comparison with neutral pH growth at any density.

Example 4

Construction of 75-15 Cells

A fusion protein denoted TK75-15 was engineered to express influenza HA protein on the cell wall using the Aga2 sequence, driven by the TEF2 promoter. In this construct, the protein was constructed with the HA sequence C-terminal to the Aga2 sequence. This protein, when expressed in cells that also express Aga1p (in this case, driven by the CUP1 promoter), localizes to the outer cell wall of the yeast cell, as well as to the cytosol. The fusion protein comprising the influenza HA antigen is a single polypeptide with the following sequence elements fused in frame from N- to C-terminus (the amino acid sequence of the fusion protein being represented herein by SEQ ID NO:1): 1) the full length S. cerevisiae Aga2 protein sequence (positions 1 to 87 of SEQ ID NO:1), including its natural 18 amino acid ER-targeting signal sequence (positions 1 to 18 of SEQ ID NO:1; 2) a spacer to separate the Aga2 from the HA body (positions 88 and 89); 3) influenza HA protein lacking its signal sequence (positions 90 to 600 of SEQ ID NO:1), and lacking 36 C-terminal residues of HA, thus eliminating its C-terminal membrane anchor and cytoplasmic tail; 4) a triglycine spacer to separate the body of HA protein from the histidine tag (positions 601-603 of SEQ ID NO:1); and 5) a C-terminal hexahistidine tag (positions 604-609 of SEQ ID NO:1). A nucleic acid sequence encoding the fusion protein of SEQ ID NO:1 is represented herein by SEQ ID NO:2. This fusion protein and the Tarmogen expressing it can be called 75-15.

The protein sequence used is as follows (SEQ ID NO:1):

```
MQLLRCFSIFSVIASVLAQELTTICEQIPSPTLESTPYSLSTTTILANGK      50

AMQGVFEYYKSVTFVSNCGSHPSTTSKGSPINTQYVFTSDTICIGYHANN     100

STDTVDTVLEKNVTVTHSVNLLEDSHNGKLCRLKGIAPLQLGKCNIAGWL     150

LGNPECDPLLPVRSWSYIVETPNSENGICYPGDFIDYEELREQLSSVSSF     200

ERFEIFPKESSWPNHNTNGVTAACSHEGKSSFYRNLLWLTEKEGSYPKLK     250

NSYVNKKGKEVLVLWGIHHPSNSKEQQNLYQNENAYVSVVTSNYNRRFTP     300

EIAERPKVRDQAGRMNYYWTLLKPGDTIIFEANGNLIAPMYAFALSRGFG     350

SGIITSNASMHECNTKCQTPLGAINSSLPYQNIHPVTIGERPKYVRSAKL     400

RMVTGLRNIPSIQSRGLFGAIAGFIEGGWTGMIDGWYGYHHQNEQGSGYA     450

ADQKSTQNAINGITNKVNTVIEKMNIQFTAVGKEFNKLEKRMENLNKKVD     500

DGFLDIWTYNAELLVLLENERTLDFHDSNMKNLYEKVKSQLKNNAKEIGN     550

GCFEFYHKCDNECMESVRNGTYDYPKYSEESKLNREKVDGVKLESMGIYQ     600

GGGHHHHHH*
```

The corresponding nucleic acid sequence is as follows (SEQ ID NO:2):

```
  1   ATGCAGTTAC TTCGCTGTTT TTCAATATTT TCTGTTATTG
      CTTCAGTTTT

51   AGCACAGGAA CTGACAACTA TATGCGAGCA AATCCCCTCA
      CCAACTTTAG

101   AATCGACGCC GTACTCTTTG TCAACGACTA CTATTTTGGC
      CAACGGGAAG

151   GCAATGCAAG GAGTTTTTGA ATATTACAAA TCAGTAACGT
      TTGTCAGTAA

201   TTGCGGTTCT CACCCCTCAA CAACTAGCAA AGGCAGCCCC
      ATAAACACAC

251   AGTATGTTTT TACTAGTGAC ACAATATGTA TAGGCTACCA
      TGCGAACAAT

301   TCAACCGACA CTGTTGACAC AGTACTCGAG AAGAATGTGA
      CAGTGACACA

351   CTCTGTTAAC CTGCTCGAAG ACAGCCACAA CGGAAAACTA
      TGTAGATTAA

401   AAGGAATAGC CCCACTACAA TTGGGGAAAT GTAACATCGC
      CGGATGGCTC

451   TTGGGGAATC CAGAATGCGA CCCACTGCTT CCAGTGAGAT
      CATGGTCCTA

501   CATTGTAGAA ACACCAAACT CTGAGAATGG AATATGTTAT
      CCAGGAGATT
```

-continued

```
  551  TCATCGACTA TGAGGAGCTG AGGGAGCAAT TGAGCTCAGT
       GTCATCATTC

601  GAAAGATTCG AAATATTTCC CAAAGAAAGC TCATGGCCCA
       ACCACAACAC

651  AAACGGAGTA ACGGCAGCAT GCTCCCATGA GGGGAAAAGC
       AGTTTTTACA

701  GAAATTTGCT ATGGCTGACG GAGAAGGAGG GCTCATACCC
       AAAGCTGAAA

751  AATTCTTATG TGAACAAAAA AGGGAAAGAA GTCCTTGTAC
       TGTGGGGTAT

801  TCATCACCCG TCTAACAGTA AGGAACAACA GAATCTCTAT
       CAGAATGAAA

851  ATGCTTATGT CTCTGTAGTG ACTTCAAATT ATAACAGGAG
       ATTTACCCCG

901  GAAATAGCAG AAAGACCCAA AGTAAGAGAT CAAGCTGGGA
       GGATGAACTA

951  TTACTGGACC TTGCTAAAAC CCGGAGACAC AATAATATTT
       GAGGCAAATG

1001  GAAATCTAAT AGCACCAATG TATGCTTTCG CACTGAGTAG
       AGGCTTTGGG

1051  TCCGGCATCA TCACCTCAAA CGCATCAATG CATGAGTGTA
       ACACGAAGTG

1101  TCAAACACCC CTGGGAGCTA TAAACAGCAG TCTCCCTTAC
       CAGAATATAC

1151  ACCCAGTCAC AATAGGAGAG CGCCCAAAAT ACGTCAGGAG
       TGCCAAATTG

1201  AGGATGGTTA CAGGACTAAG GAACATTCCG TCCATTCAAT
       CCAGAGGTCT

1251  ATTTGGAGCC ATTGCCGGTT TTATTGAAGG GGGATGGACT
       GGAATGATAG

1301  ATGGATGGTA TGGTTATCAT CATCAGAATG AACAGGGATC
       AGGCTATGCA

1351  GCGGATCAAA AAAGCACACA AAATGCCATT AACGGGATTA
       CAAACAAGGT

1401  GAACACTGTT ATCGAGAAAA TGAACATTCA ATTCACAGCT
       GTGGGTAAAG

1451  AATTCAACAA ATTAGAAAAA AGGATGGAAA ATTTAAATAA
       AAAAGTTGAT

1501  GATGGATTTC TGGACATTTG GACATATAAT GCAGAATTGT
       TAGTTCTACT

1551  GGAAAATGAA AGGACTCTGG ACTTCCATGA CTCAAATATG
       AAGAATCTGT

1601  ATGAGAAAGT AAAAAGCCAA TTAAAGAATA ATGCCAAAGA
       AATCGGAAAT

1651  GGATGTTTTG AGTTCTACCA CAAGTGTGAC AATGAATGCA
       TGGAAAGTGT

1701  AAGAAATGGG ACTTATGATT ATCCCAAATA TTCAGAAGAG
       TCAAAGTTGA

1751  ACAGGGAAAA GGTAGATGGA GTGAAATTGG AATCAATGGG
       GATCTATCAG

1801  GGTGGCGGGC ATCACCATCA CCATCACTAG TGA
```

Example 5

The Effect of Different Buffers (pH 6.5 Media) on 75-15 Cell Growth and Culture pH Different buffering agents were tested on 75-15 cells to determine its effect on cell growth and also the effect on the culture pH. These buffers are shown in FIG. 3 and included succinate, citrate, and carbonate. None of the buffers caused precipitate to form. All of the buffers used dissolved well in standard growth media. The pH of all test cultures was adjusted to pH 6.5 prior to inoculation with yeast. Cultures were then grown in shake flasks at 30° C. for up to 15 hours. There was minimal to no growth seen when the cells were grown in carbonate buffer. As can be seen in FIG. 3, the use of different buffering agents affected growth rates. The growth was faster in neutral pH (at least pH 5.5). In particular, the media with succinate buffer performed the best in terms of doubling time (~2.5 hr doubling time). In contrast, if the yeast cells were grown in pH less than 5.5 (more acidic conditions), then the doubling time was slower at ~3.5 hr. Citrate had similar doubling time (~3.5 hrs). Citrate at 0.05M had a greater buffering capacity than succinate at 0.02M. In these experiments, all the cultures received 0.35 mM copper for induction of expression.

Example 6

Effect of Various Buffering Agents on Cell Lysis

FIG. 4 shows the results from experiments conducted with different buffering agents such as succinate and citrate. Cultures were grown as described in Example 1. The ability of the yeast to be lysed by glucanase was measured using the lysis assay protocol above. The yeast in the control culture (media pH~5.2) showed less efficient lysis by glucanase as the cell density increased (cell densities indicated by the number after the dash, as described above for FIG. 2). However, for both succinate and citrate buffered media, the cell density at time of harvest did not have any effect on the ability of the yeast to be lysed by cell wall digestive enzymes in the lysis assay described above. The yeast in the succinate and citrate buffered media remained susceptible to lysis at increasing cell densities (e.g., 0.5 YU/ml, 0.9 YU/ml and 2.1 or 2.2 YU/ml).

Example 7

Media Formulation Study

The contribution of other agents added to the yeast culture media was tested and the results are shown in FIG. 5. U2 or U4 refers to the basic media composition. Since protein expression is under control of the copper-inducible CUP1 promoter, 0.35 mM copper is added to the media for yeast cells to be induced to express HA protein. Soytone (Soy in FIG. 5), is a commercially available complex mixture of nutrients derived by peptic digestion of soybeans. The addition of soytone gave fastest growth and highest yield (30YU/mL). The use of 0.08M succinic acid showed better buffering capacity. Cells were grown at 30° C. for the times indicated on the x-axis.

FIG. 6 shows the results for media formulation study that used Guava Technologies for determination of cell viability. Yeast strain 75-15 in which express copper-inducible Aga2-HA were grown at 30° C. in shake flasks. When copper is added to the culture, the Aga2-HA protein is expressed and will show up on the cell surface, which represents the number of yeast cells that show HA on the surface (% positive signal). Cell viability can also be determined using other methods (e.g., hemacytometer or Trypan blue). The highest signal was observed with U2, even at a cell density of 8YU/mL, which is past the cell density at which cells tend to slow down in its growth rate. The cultures using soytone showed clear effect of cell density, with high densities showing a decline in protein. The use of U4 gave low signal overall. These results also demonstrate the accessibility of detection because of the effects pH has on the cell wall and the ability of HA-specific antibodies to detect the surface expressed protein.

Additional experiments were conducted using different concentration of soytone. FIG. 7 illustrates the results. No different in growth or pH was observed between 0.5 g/l and 1 g/l soytone. Faster growth was observed in U4-YNB media than in U2 media.

Example 8

Difference in HA Accessibility when Yeast are Grown at Neutral pH Conditions

The accessibility of particular antigens to interactions from other agents, such as an antibody for detection, was assessed using varying pH levels of the media. FIG. 8 shows an immunoblot assay of releasable influenza hemagglutin (HA) from intact yeast when the yeast cells were grown at pH less than 5 and also when yeast were grown at a pH of more than 6. Yeast grown at neutral pH makes the surface displayed HA much more accessible to antibody detection, as determined flow cytometry staining, both in number of cells that express HA and the amount of HA per cell. In addition, the yeast grown at neutral pH were easier to manipulate for the release of the disulfide-bonded HA by treatment with dithiothreitol (disulfide reducing agent).

Example 9

The Effect of Neutral pH on Cytokine Production

The effect of culturing yeast at neutral pH on cytokine production was examined by using dendritic cells (DC) loaded with YVEC yeast (not expressing a heterologous antigen) grown in media where the pH was or was not maintained above pH 5.5. Mouse bone marrow-derived dendritic cells were loaded with 10 yeast per DC by incubating together in RPMI media for 48 hr at 37° C. Supernatants were then analyzed for secreted cytokines. FIG. 9 shows the results of these experiments. The lower panel show that there is a marked increase of IFN-gamma secretion from dendritic cells loaded with the yeast are grown at a neutral pH (i.e., at least 5.5 or higher) that is absent when the yeast are grown in media where the pH was allowed to drop lower than 5.5.

What is claimed is:

1. A method for growing yeast from *Saccharomyces cerevisiae* that express a heterologous antigen on its surface, internally, or both on its surface and internally, comprising culturing the yeast in a medium that has been maintained at a pH of between 5.5 and 8 for at least 90% of the time the yeast are in culture, and further comprising formulating the antigen-expressing yeast for administration to an individual.

2. The method of claim 1, further comprising formulating the yeast with a pharmaceutically acceptable excipient.

3. The method of claim 1, wherein the yeast have been cultured in a medium that has been maintained at a pH of between 6 and 8 for at least 90% of the time the yeast are in culture.

4. The method of claim 1, wherein the yeast are cultured in a medium wherein the pH of the medium does not drop below pH 5.5 while the yeast are in culture.

5. The method of claim 1, wherein the medium is buffered with a buffering agent.

6. The method of claim 1, wherein the medium is buffered with Bis-Tris.

7. The method of claim 1, wherein the medium is buffered with succinate or succinic acid.

8. The method of claim 1, wherein the medium is buffered with citrate.

9. The method of claim 1, wherein the medium is buffered with phosphate.

10. The method of claim 1, wherein the heterologous antigen is expressed on the surface of the yeast.

11. The method of claim 1, further comprising lyophilizing the yeast.

12. The method of claim 1, wherein the medium is U2 medium or UL2 medium.

13. A method for growing yeast from *Saccharomyces* that express a heterologous antigen on its surface, internally, or both on its surface and internally, comprising culturing the yeast in a medium that has been maintained at a pH of between 5.5 and 8 for the entire time the yeast are in culture, and further comprising formulating the antigen-expressing yeast for administration to an individual.

14. The method of claim 13, wherein the medium has been maintained at a pH of between 6 and 8 for the entire time the yeast are in culture.

15. The method of claim 13, wherein the medium is buffered with a buffering agent.

16. The method of claim 13, wherein the medium is buffered with Bis-Tris.

17. The method of claim 13, wherein the medium is buffered with succinate or succinic acid.

18. The method of claim 13, wherein the medium is buffered with citrate.

19. The method of claim 13, wherein the medium is buffered with phosphate.

20. The method of claim 13, further comprising lyophilizing the yeast.

21. A method for growing yeast from *Saccharomyces* that express a heterologous antigen on its surface, internally, or both on its surface and internally, comprising growing and maintaining the yeast in a buffered medium, wherein the pH of the medium does not drop below pH 5.5 from the start of yeast growth to harvest of the yeast, and further comprising formulating the antigen-expressing yeast for administration to an individual.

22. The method of claim 21, wherein the medium is buffered with a buffering agent.

23. The method of claim 21, further comprising lyophilizing the yeast.

* * * * *

SEQUENCE LISTING

```
<160> NUMBER OF SEQ ID NOS: 2

<210> SEQ ID NO 1
<211> LENGTH: 609
<212> TYPE: PRT
<213> ORGANISM: Artificial
<220> FEATURE:
<223> OTHER INFORMATION: Synthetic Construct

<400> SEQUENCE: 1

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Thr Ser Asp Thr Ile Cys Ile Gly Tyr
                85                  90                  95

His Ala Asn Asn Ser Thr Asp Thr Val Asp Thr Val Leu Glu Lys Asn
            100                 105                 110

Val Thr Val Thr His Ser Val Asn Leu Leu Glu Asp Ser His Asn Gly
        115                 120                 125

Lys Leu Cys Arg Leu Lys Gly Ile Ala Pro Leu Gln Leu Gly Lys Cys
    130                 135                 140

Asn Ile Ala Gly Trp Leu Leu Gly Asn Pro Glu Cys Asp Pro Leu Leu
145                 150                 155                 160

Pro Val Arg Ser Trp Ser Tyr Ile Val Glu Thr Pro Asn Ser Glu Asn
```

-continued

```
            165                 170                 175
Gly Ile Cys Tyr Pro Gly Asp Phe Ile Asp Tyr Glu Glu Leu Arg Glu
            180                 185                 190
Gln Leu Ser Ser Val Ser Ser Phe Glu Arg Phe Glu Ile Phe Pro Lys
            195                 200                 205
Glu Ser Ser Trp Pro Asn His Asn Thr Asn Gly Val Thr Ala Ala Cys
            210                 215                 220
Ser His Glu Gly Lys Ser Ser Phe Tyr Arg Asn Leu Leu Trp Leu Thr
225                 230                 235                 240
Glu Lys Glu Gly Ser Tyr Pro Lys Leu Lys Asn Ser Tyr Val Asn Lys
            245                 250                 255
Lys Gly Lys Glu Val Leu Val Leu Trp Gly Ile His His Pro Ser Asn
            260                 265                 270
Ser Lys Glu Gln Gln Asn Leu Tyr Gln Asn Glu Asn Ala Tyr Val Ser
            275                 280                 285
Val Val Thr Ser Asn Tyr Asn Arg Arg Phe Thr Pro Glu Ile Ala Glu
            290                 295                 300
Arg Pro Lys Val Arg Asp Gln Ala Gly Arg Met Asn Tyr Tyr Trp Thr
305                 310                 315                 320
Leu Leu Lys Pro Gly Asp Thr Ile Ile Phe Glu Ala Asn Gly Asn Leu
            325                 330                 335
Ile Ala Pro Met Tyr Ala Phe Ala Leu Ser Arg Gly Phe Gly Ser Gly
            340                 345                 350
Ile Ile Thr Ser Asn Ala Ser Met His Glu Cys Asn Thr Lys Cys Gln
            355                 360                 365
Thr Pro Leu Gly Ala Ile Asn Ser Ser Leu Pro Tyr Gln Asn Ile His
            370                 375                 380
Pro Val Thr Ile Gly Glu Arg Pro Lys Tyr Val Arg Ser Ala Lys Leu
385                 390                 395                 400
Arg Met Val Thr Gly Leu Arg Asn Ile Pro Ser Ile Gln Ser Arg Gly
            405                 410                 415
Leu Phe Gly Ala Ile Ala Gly Phe Ile Glu Gly Gly Trp Thr Gly Met
            420                 425                 430
Ile Asp Gly Trp Tyr Gly Tyr His His Gln Asn Glu Gln Gly Ser Gly
            435                 440                 445
Tyr Ala Ala Asp Gln Lys Ser Thr Gln Asn Ala Ile Asn Gly Ile Thr
            450                 455                 460
Asn Lys Val Asn Thr Val Ile Glu Lys Met Asn Ile Gln Phe Thr Ala
465                 470                 475                 480
Val Gly Lys Glu Phe Asn Lys Leu Glu Lys Arg Met Glu Asn Leu Asn
            485                 490                 495
Lys Lys Val Asp Asp Gly Phe Leu Asp Ile Trp Thr Tyr Asn Ala Glu
            500                 505                 510
Leu Leu Val Leu Leu Glu Asn Glu Arg Thr Leu Asp Phe His Asp Ser
            515                 520                 525
Asn Met Lys Asn Leu Tyr Glu Lys Val Lys Ser Gln Leu Lys Asn Asn
            530                 535                 540
Ala Lys Glu Ile Gly Asn Gly Cys Phe Glu Phe Tyr His Lys Cys Asp
545                 550                 555                 560
Asn Glu Cys Met Glu Ser Val Arg Asn Gly Thr Tyr Asp Tyr Pro Lys
            565                 570                 575
Tyr Ser Glu Glu Ser Lys Leu Asn Arg Glu Lys Val Asp Gly Val Lys
            580                 585                 590
```

Leu Glu Ser Met Gly Ile Tyr Gln Gly Gly Gly His His His His His
        595                 600                 605
His

<210> SEQ ID NO 2
<211> LENGTH: 1833
<212> TYPE: DNA
<213> ORGANISM: Artificial
<220> FEATURE:
<223> OTHER INFORMATION: Synthetic Construct

<400> SEQUENCE: 2

| | | | | |
|---|---|---|---|---|
| atgcagttac | ttcgctgttt | ttcaatattt | tctgttattg | cttcagtttt | agcacaggaa | 60 |
| ctgacaacta | tatgcgagca | aatcccctca | ccaactttag | aatcgacgcc | gtactctttg | 120 |
| tcaacgacta | ctattttggc | caacgggaag | gcaatgcaag | gagttttga | atattacaaa | 180 |
| tcagtaacgt | ttgtcagtaa | ttgcggttct | caccccctcaa | caactagcaa | aggcagcccc | 240 |
| ataaacacac | agtatgtttt | tactagtgac | acaatatgta | taggctacca | tgcgaacaat | 300 |
| tcaaccgaca | ctgttgacac | agtactcgag | aagaatgtga | cagtgacaca | ctctgttaac | 360 |
| ctgctcgaag | acagccacaa | cggaaaacta | tgtagattaa | aggaatagc | cccactacaa | 420 |
| ttggggaaat | gtaacatcgc | cggatggctc | ttggggaatc | cagaatgcga | cccactgctt | 480 |
| ccagtgagat | catggtccta | cattgtagaa | acaccaaact | ctgagaatgg | aatatgttat | 540 |
| ccaggagatt | tcatcgacta | tgaggagctg | agggagcaat | tgagctcagt | gtcatcattc | 600 |
| gaaagattcg | aaatatttcc | caaagaaagc | tcatggccca | accacaacac | aaacggagta | 660 |
| acggcagcat | gctcccatga | ggggaaaagc | agttttttaca | gaaatttgct | atggctgacg | 720 |
| gagaaggagg | gctcataccc | aaagctgaaa | aattcttatg | tgaacaaaaa | agggaaagaa | 780 |
| gtccttgtac | tgtggggtat | tcatcacccg | tctaacagta | aggaacaaca | gaatctctat | 840 |
| cagaatgaaa | atgcttatgt | ctctgtagtg | acttcaaatt | ataacaggag | atttaccccg | 900 |
| gaaatagcag | aaagacccaa | agtaagagat | caagctggga | ggatgaacta | ttactggacc | 960 |
| ttgctaaaac | ccggagacac | aataatattt | gaggcaaatg | gaaatctaat | agcaccaatg | 1020 |
| tatgctttcg | cactgagtag | aggctttggg | tccggcatca | tcacctcaaa | cgcatcaatg | 1080 |
| catgagtgta | acacgaagtg | tcaaacaccc | ctgggagcta | taaacagcag | tctcccttac | 1140 |
| cagaatatac | acccagtcac | aataggagag | cgcccaaaat | acgtcaggag | tgccaaattg | 1200 |
| aggatggtta | caggactaag | gaacattccg | tccattcaat | ccagaggtct | atttggagcc | 1260 |
| attgccggtt | ttattgaagg | gggatggact | ggaatgatag | atggatggta | tggttatcat | 1320 |
| catcagaatg | aacagggatc | aggctatgca | gcggatcaaa | aaagcacaca | aaatgccatt | 1380 |
| aacgggatta | caaacaaggt | gaacactgtt | atcgagaaaa | tgaacattca | attcacagct | 1440 |
| gtgggtaaag | aattcaacaa | attagaaaaa | aggatggaaa | atttaaataa | aaaagttgat | 1500 |
| gatggatttc | tggacatttg | gacatataat | gcagaattgt | tagttctact | ggaaaatgaa | 1560 |
| aggactctgg | acttccatga | ctcaaatatg | aagaatctgt | atgagaaagt | aaaaagccaa | 1620 |
| ttaaagaata | atgccaaaga | aatcggaaat | ggatgttttg | agttctacca | caagtgtgac | 1680 |
| aatgaatgca | tggaaagtgt | aagaaatggg | acttatgatt | atcccaaata | ttcagaagag | 1740 |
| tcaaagttga | acagggaaaa | ggtagatgga | gtgaaattgg | aatcaatggg | gatctatcag | 1800 |
| ggtggcgggc | atcaccatca | ccatcactag | tga | | | 1833 |